US012385952B2

(12) United States Patent
Shirotori et al.

(10) Patent No.: US 12,385,952 B2
(45) Date of Patent: Aug. 12, 2025

(54) MAGNETIC SENSOR AND INSPECTION DEVICE

(71) Applicant: KABUSHIKI KAISHA TOSHIBA, Tokyo (JP)

(72) Inventors: Satoshi Shirotori, Yokohama (JP); Akira Kikitsu, Yokohama (JP); Yoshihiro Higashi, Komatsu (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 131 days.

(21) Appl. No.: 18/166,572

(22) Filed: Feb. 9, 2023

(65) Prior Publication Data

US 2024/0069071 A1 Feb. 29, 2024

(30) Foreign Application Priority Data

Aug. 25, 2022 (JP) ................. 2022-134113

(51) Int. Cl.
*G01R 15/20* (2006.01)
*G01R 31/382* (2019.01)

(52) U.S. Cl.
CPC ........... *G01R 15/20* (2013.01); *G01R 31/382* (2019.01)

(58) Field of Classification Search
CPC ...... A61B 5/245; G01R 15/20; G01R 15/205; G01R 31/382; G01R 33/0011; G01R 33/0094; H10N 50/10
See application file for complete search history.

(56) References Cited

U.S. PATENT DOCUMENTS 11,119,161 B2 * 9/2021 Iwasaki ............... G01R 33/098
11,432,751 B2 * 9/2022 Shirotori ............... G01R 33/09
(Continued)

FOREIGN PATENT DOCUMENTS

JP 2015-125019 A 7/2015
JP 2019-207167 A 12/2019
(Continued)

OTHER PUBLICATIONS

Xiaoming Zhang et al., "Influence of size parameters and magnetic field intensity upon the amplification characteristics of magnetic flux concentrators," AIP Advances, vol. 8, 125222, 11 pages (2018).
(Continued)

*Primary Examiner* — Vinh P Nguyen
(74) *Attorney, Agent, or Firm* — Finnegan, Henderson, Farabow, Garrett & Dunner, LLP

(57) ABSTRACT

According to one embodiment, a magnetic sensor includes a first element portion that includes a first magnetic element, a first conductive member, a first magnetic member and a first opposing magnetic member. The first magnetic element includes a first end portion and a first other end portion. A direction from the first end portion to the first other end portion is along a first direction. A second direction from the first conductive member to the first magnetic element crosses the first direction. A third direction from the first magnetic member to the first opposing magnetic member crosses a plane including the first and second directions. At least a part of the first magnetic element is between the first magnetic member and the first opposing magnetic member in position in the third direction. The first magnetic member includes a first other magnetic portion and a first magnetic portion.

20 Claims, 18 Drawing Sheets

(56) References Cited

U.S. PATENT DOCUMENTS

| | | | |
|---|---|---|---|
| 12,265,141 B2* | 4/2025 | Kikitsu | H10N 50/10 |
| 2015/0177286 A1 | 6/2015 | Fuji et al. | |
| 2019/0369172 A1 | 12/2019 | Kikitsu et al. | |
| 2021/0080519 A1 | 3/2021 | Iwasaki et al. | |
| 2022/0065955 A1* | 3/2022 | Kikitsu | G01R 33/0011 |
| 2022/0175289 A1 | 6/2022 | Shirotori et al. | |

FOREIGN PATENT DOCUMENTS

| | | |
|---|---|---|
| JP | 2021-47169 A | 3/2021 |
| JP | 2022-37688 A | 3/2022 |
| JP | 2022-88883 | 6/2022 |

OTHER PUBLICATIONS

Japan Patent Office, Office Action in JP Patent App. No. 2022-134113 (Jun. 16, 2025).

* cited by examiner

MAGNETIC SENSOR AND INSPECTION DEVICE

CROSS-REFERENCE TO RELATED APPLICATIONS

This application is based upon and claims the benefit of priority from Japanese Patent Application No. 2022-134113, filed on Aug. 25, 2022; the entire contents of which are incorporated herein by reference.

FIELD

Embodiments described herein generally relate to a magnetic sensor and an inspection device.

BACKGROUND

There is a magnetic sensor using a magnetic layer. There is an inspection device using a magnetic sensor. Magnetic sensors are desired to have high detection sensitivity.

DETAILED DESCRIPTION

Figure 1A:
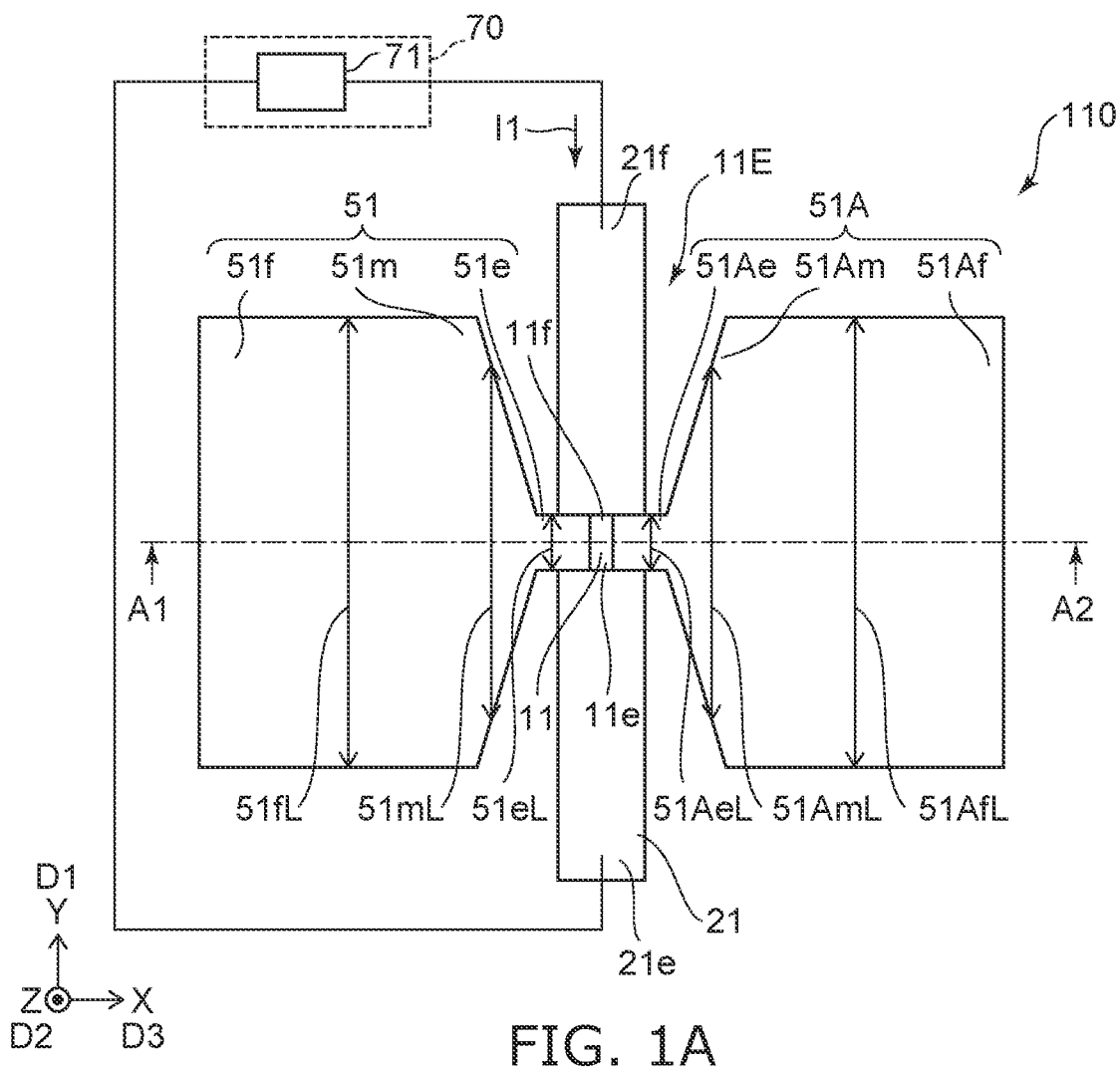
FIGS. 1A and 1B are schematic views illustrating a magnetic sensor according to a first embodiment.

According to one embodiment, a magnetic sensor includes a first element portion. The first element portion includes a first magnetic element, a first conductive member, a first magnetic member and a first opposing magnetic member. The first magnetic element includes a first end portion and a first other end portion. A direction from the first end portion to the first other end portion is along a first direction. A second direction from the first conductive member to the first magnetic element crosses the first direction. A third direction from the first magnetic member to the first opposing magnetic member crosses a plane including the first direction and the second direction. A position of at least a part of the first magnetic element in the third direction is between a position of the first magnetic member in the third direction and a position of the first opposing magnetic member in the third direction. The first magnetic member includes a first other magnetic portion and a first magnetic portion. A direction from the first other magnetic portion to the first magnetic portion is along the third direction. A first other magnetic portion length along the first direction of the first other magnetic portion is longer than a first magnetic portion length along the first direction of the first magnetic portion. The first conductive member overlaps the first magnetic portion in the second direction. The first conductive member does not overlap the first other magnetic portion in the second direction.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously in an antecedent drawing are marked with like reference numerals, and a detailed description is omitted as appropriate.

First Embodiment

Figure 1B:
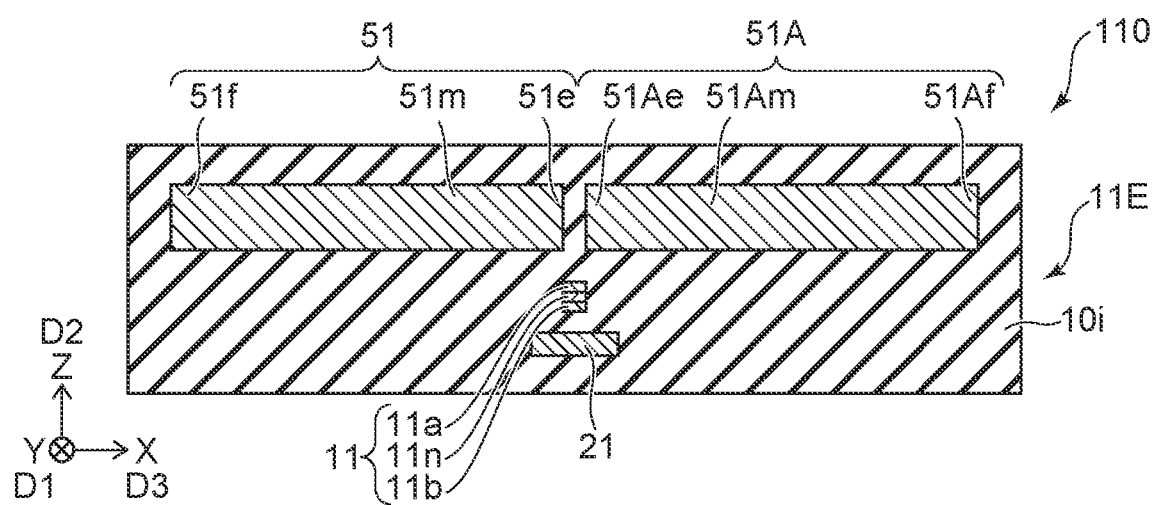

FIGS. 1A and 1B are schematic views illustrating a magnetic sensor according to the first embodiment.

FIG. 1A is a plan view. FIG. 1B is a cross-sectional view taken along the line A1-A2 of FIG. 1A.

As shown in FIGS. 1A and 1B, a magnetic sensor 110 according to the embodiment includes a first element portion 11E. The first element portion 11E includes a first magnetic element 11, a first conductive member 21, a first magnetic member 51 and a first opposing magnetic member 51A. The first magnetic element 11 includes a first end portion 11e and a first other end portion 11f. A direction from the first end portion 11e to the first other end portion 11f is along a first direction D1.

Let the first direction D1 be a Y-axis direction. One direction perpendicular to the Y-axis direction is defined as a Z-axis direction. A direction perpendicular to the Y-axis direction and the Z-axis direction is defined as an X-axis direction.

As shown in FIG. 1B, the second direction D2 from the first conductive member 21 to the first magnetic element 11 crosses the first direction D1.

A third direction D3 from the first magnetic member 51 to the first opposing magnetic member 51A crosses a plane including the first direction D1 and the second direction D2. A position of at least part of the first magnetic element 11 in the third direction D3 is between a position of the first magnetic member 51 in the third direction D3 and a position of the first opposing magnetic member 51A in the third direction D3.

For example, a length of the first magnetic element 11 along the first direction D1 is longer than a length of the first magnetic element 11 along the third direction D3. For example, a length of the first magnetic element 11 along the first direction D1 is also longer than the length of the first magnetic element 11 along the second direction D2. Thereby, the magnetization of the magnetic layer included in the first magnetic element 11 is easily stabilized.

As shown in FIG. 1A, the first magnetic member 51 includes a first other magnetic portion 51f and a first magnetic portion 51e. The direction from the first other magnetic portion 51f to the first magnetic portion 51e is along the third direction D3. The length (width) of the first other magnetic portion 51f in the first direction D1 is defined as a first other magnetic portion length 51fL. The length (width) of the first magnetic portion 51e in the first direction D1 is defined as a first magnetic portion length 51eL. The first other magnetic portion length 51fL is longer than the first magnetic portion length 51eL. The first other magnetic portion 51f is, for example, a wide portion. The first magnetic portion 51e is, for example, a narrow portion.

As shown in FIGS. 1A and 1B, the first conductive member 21 overlaps the first magnetic portion 51e in the second direction D2. The first conductive member 21 does not overlap the first other magnetic portion 51f in the second direction D2.

For example, the magnetic field around the first element portion 11E is collected by the first magnetic member 51 and the first opposing magnetic member 51A. The collected magnetic field is applied to the first magnetic element 11. The first magnetic member 51 and the first opposing magnetic member 51A function, for example, as an MFC (Magnetic Flux Concentrator). The magnetic field around the first element portion 11E includes the detection target magnetic field.

As will be described later, a first current I1 (see FIG. 1A) including an AC component is supplied to the first conductive member 21. A magnetic field based on the first current I1 is also collected by the first magnetic member 51 and the first opposing magnetic member 51A. The concentrated magnetic field based on the first current I1 is effectively applied to the first magnetic element 11. For example, high sensitivity is obtained. A magnetic sensor capable of detection with high sensitivity can be provided.

In the embodiment, the first conductive member 21 overlaps the first magnetic portion 51e and does not overlap the first other magnetic portion 51f. As a result, a magnetic field based on the first current I1 is effectively applied to the first magnetic element 11. Noise is suppressed by that the first conductive member 21 overlaps the narrow portion and does not overlap the wide portion.

As shown in FIG. 1A, there is a portion whose width changes between the first other magnetic portion 51f and the first magnetic portion 51e. Noise increases when the first conductive member 21 overlaps the portion where the width changes. It is considered that this is caused by non-uniformity of the magnetic domains included in the magnetic layer in the portion where the width changes. It is considered that the magnetic domains are uniform in the narrow portion. Noise is suppressed by overlapping the first conductive member 21 the narrow portion. High sensitivity can be obtained while suppressing noise. A magnetic sensor capable of detection with high sensitivity can be provided.

As shown in FIG. 1A, the first magnetic member 51 may further include a first intermediate magnetic portion 51m. The first intermediate magnetic portion 51m is between the first other magnetic portion 51f and the first magnetic portion 51e in the third direction D3. A length of the first intermediate magnetic portion 51m along the first direction D1 is defined as a first intermediate magnetic portion length of 51mL. The first intermediate magnetic portion length 51mL is between the first other magnetic portion length 51fL and the first magnetic portion length 51eL. The first intermediate magnetic portion length 51mL varies in the third direction D3. The first intermediate magnetic portion 51m is a portion whose width changes.

The rate of change in the third direction D3 of the first magnetic portion length 51eL is lower than the rate of change in the third direction D3 of the first intermediate magnetic portion length 51mL. The rate of change of the first magnetic portion length 51eL in the third direction D3 may be substantially zero. For example, the first magnetic portion length 51eL may be substantially constant. The first conductive member 21 does not overlap the first intermediate magnetic portion 51m in the second direction D2. Thereby, noise can be suppressed.

The rate of change in the third direction D3 of the first other magnetic portion length 51fL is lower than the rate of change in the third direction D3 of the first intermediate magnetic portion length 51mL. The rate of change in the third direction D3 of the first other magnetic portion length 51fL may be substantially zero. For example, the first other magnetic portion length 51fL may be substantially constant.

In this example, the first intermediate magnetic portion 51m changes linearly in the third direction D3. The change in the third direction D3 of the first intermediate magnetic portion 51m may be curved-like. The length of the first intermediate magnetic portion 51m along the third direction D3 may be short. The first intermediate magnetic portion 51m may change sharply in the third direction D3.

As shown in FIG. 1A, the first opposing magnetic member 51A includes a first opposing other magnetic portion 51Af and a first opposing magnetic portion 51Ae. The direction from the first opposing magnetic portion 51Ae to the first opposing other magnetic portion 51Af is along the third direction D3. A length (width) of the first opposing other magnetic portion 51Af in the first direction D1 is defined as a first opposing other magnetic portion length 51AfL. A length (width) of the first opposing magnetic portion 51Ae in the first direction D1 is defined as a first opposing magnetic portion length 51AeL. The first opposing other magnetic portion length 51AfL is longer than the first opposing magnetic portion length 51AeL.

As shown in FIGS. 1A and 1B, the first conductive member 21 overlaps the first opposing magnetic portion 51Ae in the second direction D2. The first conductive member 21 does not overlap the first opposing other magnetic portion 51Af in the second direction D2.

As shown in FIG. 1A, the first opposing magnetic member 51A may further include a first opposing intermediate magnetic portion 51Am. The first opposing intermediate magnetic portion 51Am is located between the first opposing other magnetic portion 51Af and the first opposing magnetic portion 51Ae in the third direction D3. The length of the first opposing intermediate magnetic portion 51Am along the first direction D1 is defined as a first opposing intermediate magnetic portion length 51AmL. The first opposing intermediate magnetic portion length 51AmL is between the first opposing other magnetic portion length 51AfL and the first opposing magnetic portion length 51AeL. The first opposing intermediate magnetic portion length 51AmL changes in the third direction D3.

The rate of change in the third direction D3 of the first opposing magnetic portion length 51AeL is lower than the rate of change in the third direction D3 of the first opposing intermediate magnetic portion length 51AmL. The rate of change in the third direction D3 of the first opposing magnetic portion length 51AeL may be substantially 0. For example, the first opposing magnetic portion length 51AeL may be substantially constant. The first conductive member 21 does not overlap the first opposing intermediate magnetic portion 51Am in the second direction D2. Thereby, noise can be suppressed.

The first opposing magnetic portion length 51AfL may be the same as the first magnetic portion length 51eL. The first opposing magnetic portion length 51AeL may be the same as the first magnetic portion length 51eL. The first opposing intermediate magnetic portion length 51AmL may be the same as the first intermediate magnetic portion length 51mL.

The intensity of the magnetic field based on the first current I1 supplied to the first conductive member 21 may be higher than the intensity of the target magnetic field, for example. The magnetic field based on the first current I1 is collected by the first magnetic member 51 and the first opposing magnetic member 51A, and is effectively applied to the first magnetic element 11, thereby suppressing, for example, the dynamic range of the system. High sensitivity can be obtained as a system.

As shown in FIG. 1B, the first magnetic element 11 includes, for example, a first magnetic layer 11a, a first opposing magnetic layer 11b, and a first non-magnetic layer 11n. The direction from the first opposing magnetic layer 11b to the first magnetic layer 11a is along the second direction D2. The first non-magnetic layer 11n is located between the first opposing magnetic layer 11b and the first magnetic layer 11a. At least one of the first magnetic layer 11a and the first opposing magnetic layer 11b may include at least one selected from the group consisting of Fe, Co, and Ni. The first non-magnetic layer 11n may include, for example, at least one selected from the group consisting of Cu and Al. The first non-magnetic layer 11n may include, for example, an insulating material.

As shown in FIG. 1B, an insulating member 10i may be provided. The insulating member 10i is provided, for example, around the first magnetic element 11, the first conductive member 21, the first magnetic member 51, and the first opposing magnetic member 51A.

As shown in FIG. 1A, the first conductive member 21 may include a first conductive portion 21e and a first other conductive portion 21f. The direction from the first conductive portion 21e to the first other conductive portion 21f is along the first direction D1.

The distance between the first conductive portion 21e and the first end portion 11e is shorter than the distance between the first conductive portion 21e and the first other end portion 11f. The distance between the first other conductive portion 21f and the first other end portion 11f is shorter than the distance between the first other conductive portion 21f and the first end portion 11e.

As shown in FIG. 1A, the magnetic sensor 110 may further include a circuit portion 70. The circuit portion 70 includes a first circuit 71. The first circuit 71 can supply a first current I1 including an AC component to the first conductive member 21. For example, the first circuit 71 is electrically connected to the first conductive portion 21e and the first other conductive portion 21f.

Figure 2:
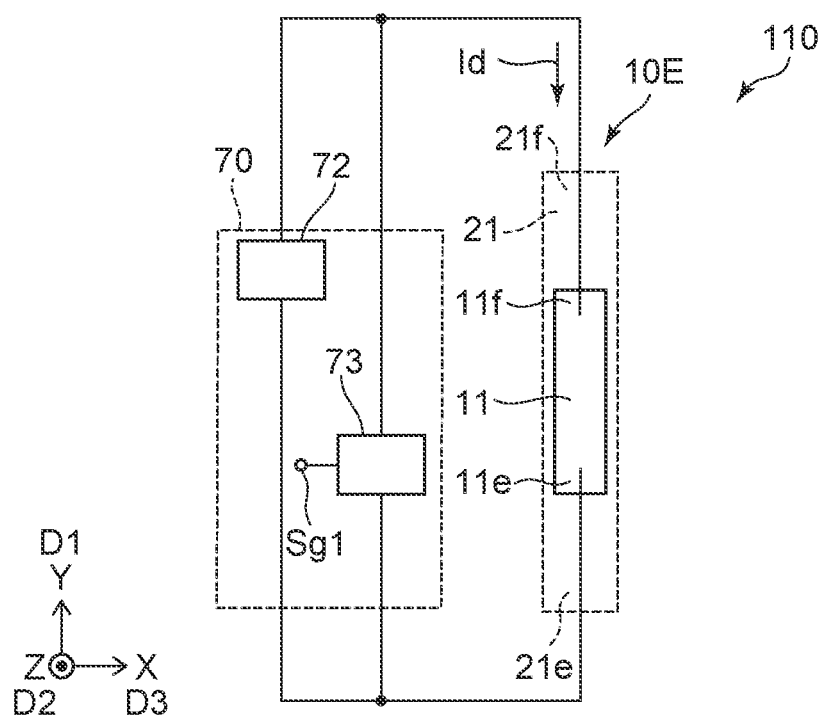
FIG. 2 is a schematic plan view illustrating a part of the magnetic sensor according to the first embodiment.

FIG. 2 is a schematic plan view illustrating a part of the magnetic sensor according to the first embodiment.

As shown in FIG. 2, the circuit portion 70 may further includes a second circuit 72 and a third circuit 73. The second circuit 72 supplies an element current Id or an element voltage to the first magnetic element 11. For example, the second circuit 72 is electrically connected to the first end portion 11e and the first other end portion 11f.

The third circuit 73 is electrically connected to the first end portion 11e and the first other end portion 11f. The third circuit 73 can output a signal Sg1 corresponding to the first electrical resistance of the first magnetic element 11.

For example, the third circuit 73 can derive a change in the first electrical resistance based on the frequency of the AC component included in the first current I1. Thereby, detection with more suppressed noise can be performed. An example of the detection operation of the magnetic sensor 110 will be described later.

Figure 3:
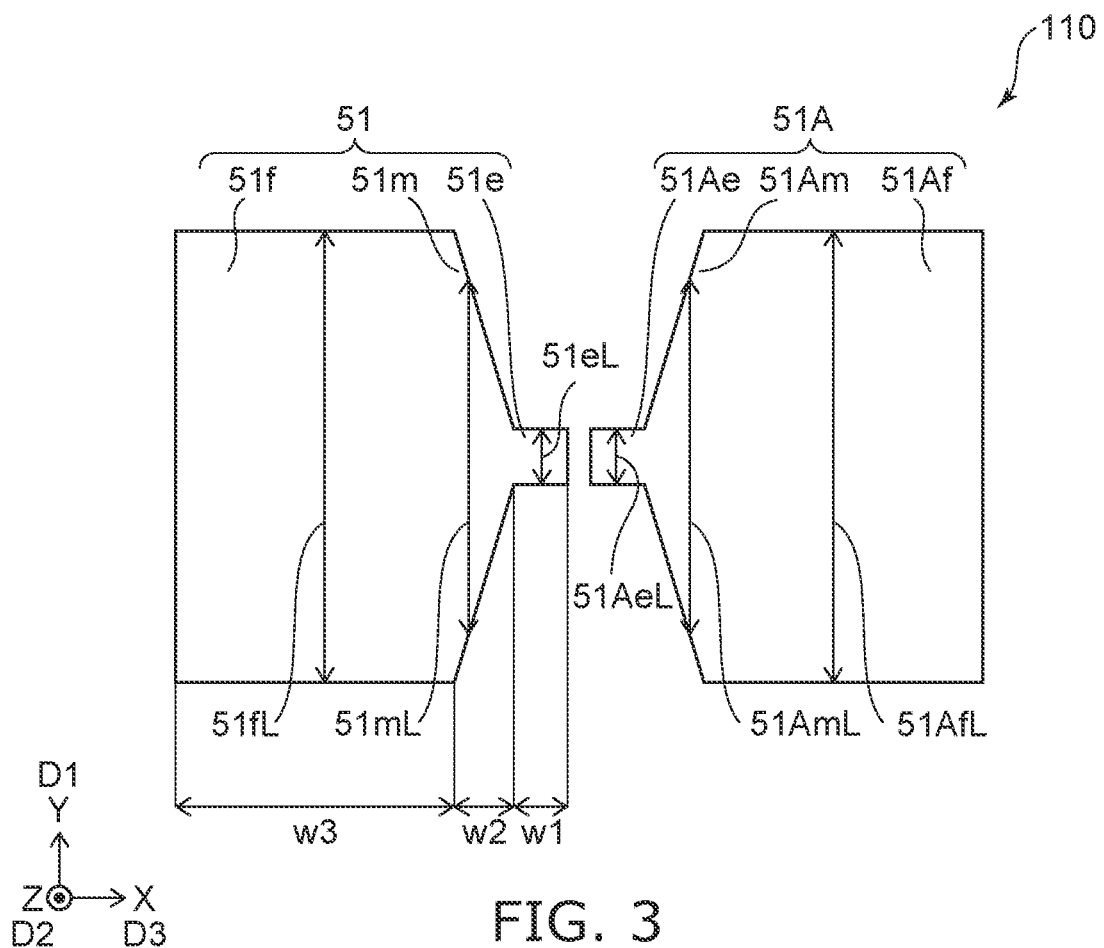
FIG. 3 is a schematic plan view illustrating a part of the magnetic sensor according to the first embodiment.

FIG. 3 is a schematic plan view illustrating a part of the magnetic sensor according to the first embodiment.

As shown in FIG. 3, a length of the first magnetic portion 51e along the third direction D3 is defined as a first length w1. The length of the first intermediate magnetic portion 51m along the third direction D3 is defined as a second length w2. A length of the first other magnetic portion 51f along the third direction D3 is defined as a third length w3.

For example, the first length w1 may be shorter than the third length w3. For example, the second length w2 may be shorter than the third length w3.

Figure 4:
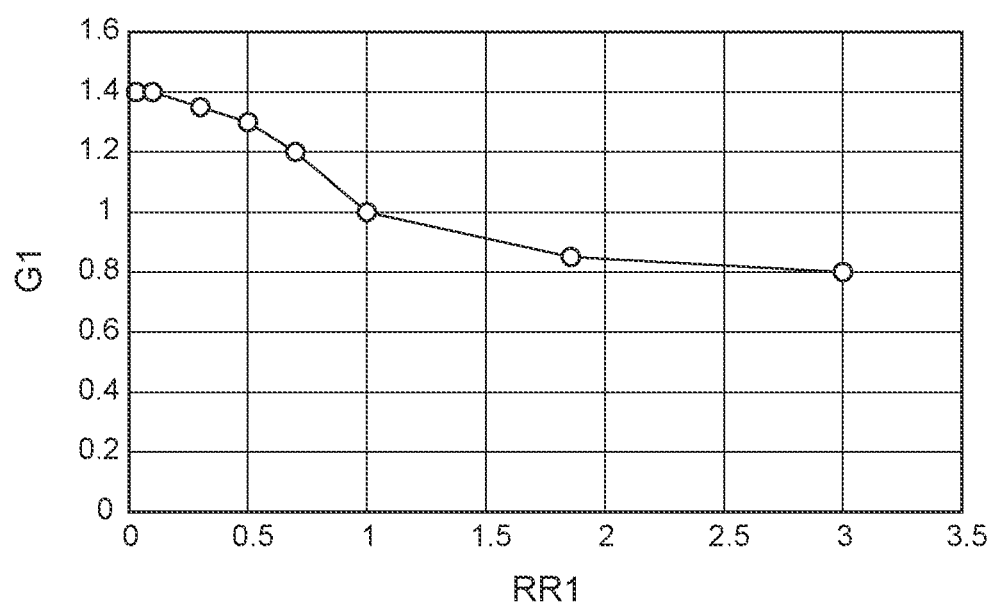
FIG. 4 is a graph illustrating characteristics of the magnetic sensor according to the first embodiment.

FIG. 4 is a graph illustrating characteristics of the magnetic sensor according to the first embodiment.

The horizontal axis of FIG. 4 is a first ratio RR1. The first ratio RR1 is a ratio of the sum of the first length w1 and the second length w2 to the third length w3. The first ratio RR1 is (w1+w2)/w3. The vertical axis of FIG. 4 is a gain G1. The gain G1 is normalized to 1 for the case in which the first magnetic portion 51e and the first intermediate magnetic portion 51m are not provided and the entire first magnetic member 51 is the first other magnetic portion 51f. In this example, the overall length (w1+w2+w3) and the second length w2 of the first magnetic member 51 are made constant, and the first length w1 and the third length w3 are changed.

As shown in FIG. 4, when the first ratio RR1 is less than 1, the gain G1 exceeds 1. In the embodiment, the first ratio RR1 is preferably less than 1. The first ratio RR1 is preferably 0.5 or less. Thereby, a higher gain G1 is obtained.

An example of a change in electrical resistance in a magnetic element will be described below.

Figure 5:
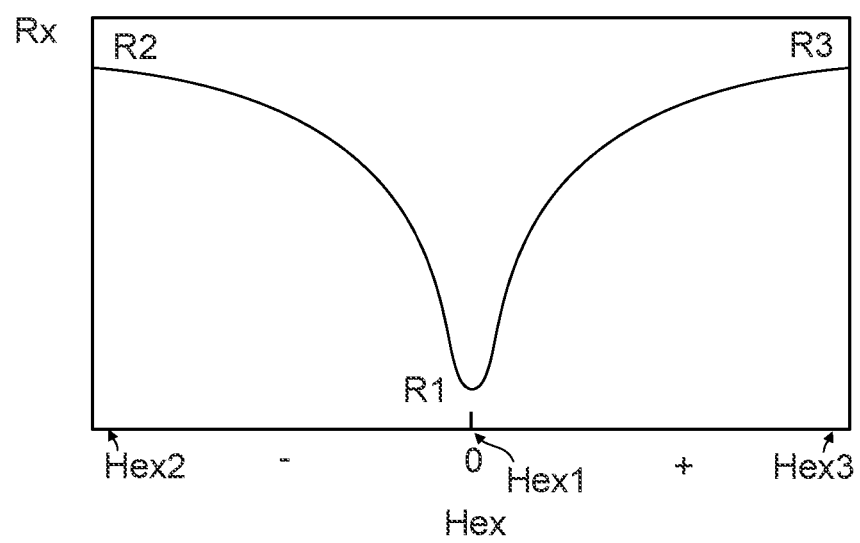
FIG. 5 is a graph illustrating the characteristics of the magnetic sensor according to the first embodiment.

FIG. 5 is a graph illustrating the characteristics of the magnetic sensor according to the first embodiment.

The horizontal axis of FIG. 5 shows the intensity of the external magnetic field Hex applied to the first magnetic element 11. The vertical axis represents the electrical resistance Rx of the first magnetic element 11. FIG. 5 corresponds to the R-H characteristic (resistance-magnetic field characteristic).

As shown in FIG. 5, the electrical resistance Rx has a characteristic of an even function with respect to the magnetic field (external magnetic field Hex, for example, a magnetic field in the X-axis direction) applied to the first magnetic element 11. For example, the electrical resistance Rx is a first value R1 when the first magnetic field Hex1 is applied to the first magnetic element 11. The electrical resistance Rx is a second value R2 when the second magnetic field Hex2 is applied to the first magnetic element 11. The electrical resistance Rx is a third value R3 when the third magnetic field Hex3 is applied to the first magnetic element 11. The absolute value of the first magnetic field Hex1 is smaller than the absolute value of the second magnetic field Hex2 and smaller than the absolute value of the third magnetic field Hex3. For example, the first magnetic field Hex1 is substantially zero. The direction of the second magnetic field Hex2 is opposite to the direction of the third magnetic field Hex3. The first value R1 is smaller than the second value R2 and smaller than the third value R3.

An example in which the first current I1 is an alternating current and does not substantially include a direct current component will be described below. The first current I1 (alternating current) is supplied to the first conductive member 21. An alternating magnetic field by the alternating current is applied to the first magnetic element 11. An example of a change in the electrical resistance Rx in such condition will be described.

Figure 6A:
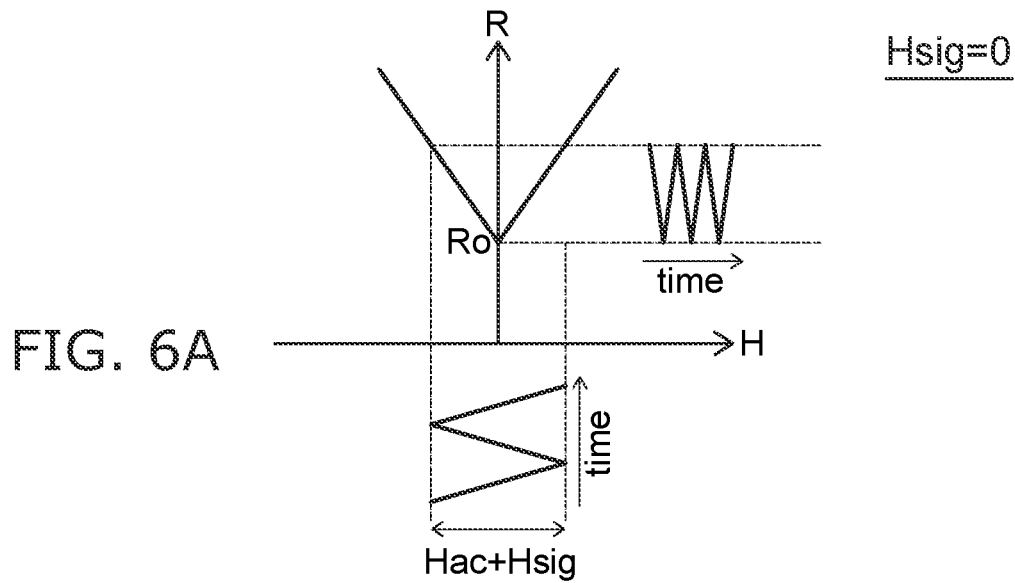
FIGS. 6A to 6C are graphs illustrating characteristics of the magnetic sensor according to the first embodiment.
Figure 6B:
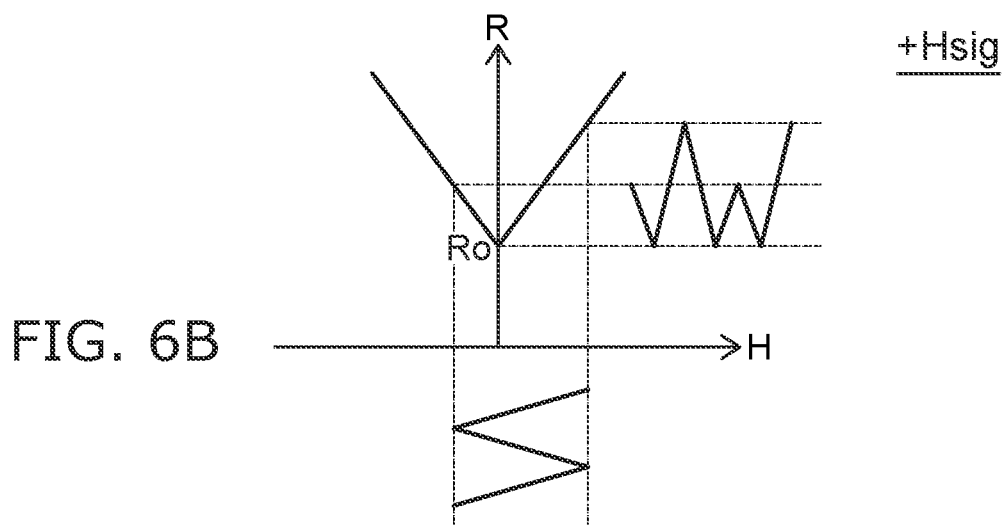
Figure 6C:
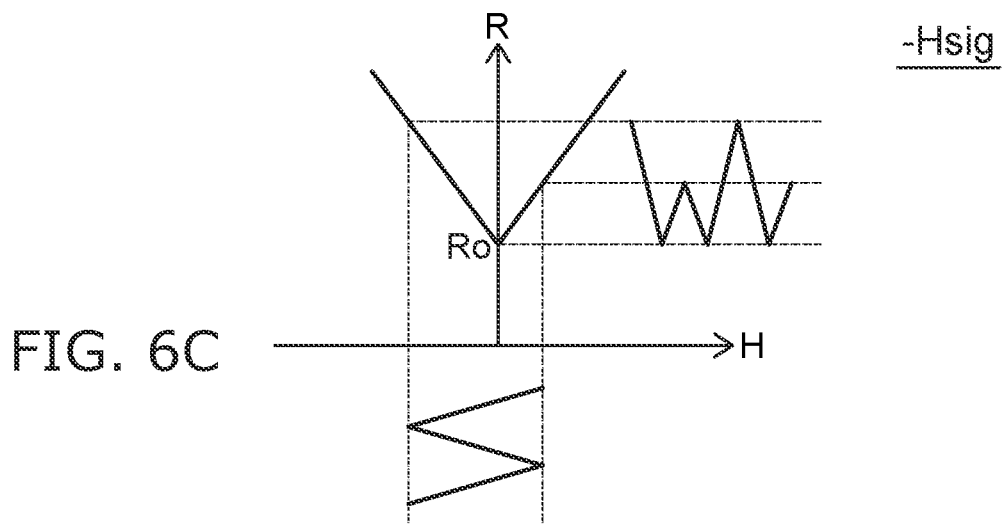

FIGS. 6A to 6C are graphs illustrating characteristics of the magnetic sensor according to the first embodiment.

FIG. 6A shows characteristics when a signal magnetic field Hsig (external magnetic field) applied to the first magnetic element 11 is 0. FIG. 6B shows characteristics when the signal magnetic field Hsig is positive. FIG. 6C shows characteristics when the signal magnetic field Hsig is negative. These figures show the relationship between the magnetic field H and the resistance R (corresponding to the electrical resistance Rx).

As shown in FIG. 6A, when the signal magnetic field Hsig is 0, the resistance R shows a characteristic symmetrical with respect to the positive and negative magnetic field H. When the AC magnetic field Hac is zero, the resistance R is a low resistance Ro. For example, the magnetization of the magnetization free layer rotates substantially similarly with respect to the positive and negative magnetic fields H. Thus, for example, a symmetrical resistance increasing characteristic is obtained. The variation of the resistance R with respect to the AC magnetic field Hac becomes the same in positive and negative polarity. The period of change of the resistance R is ½ times the period of the alternating magnetic field Hac. The change in resistance R has substantially no frequency component of the alternating magnetic field Hac.

As shown in FIG. 6B, when the positive signal magnetic field Hsig is applied, the characteristic of the resistance R shifts toward the positive magnetic field H. In the AC magnetic field Hac on the positive side, the resistance R increases. In the negative AC magnetic field Hac, the resistance R becomes small.

As shown in FIG. 6C, when the negative signal magnetic field Hsig is applied, the characteristic of the resistance R shifts toward the negative magnetic field H. In the positive AC magnetic field Hac, the resistance R decreases. In the negative AC magnetic field Hac, the resistance R increases.

When the signal magnetic field Hsig of a predetermined magnitude is applied, variations of resistances R different from each other with respect to the positive and negative of the AC magnetic field Hac occur. The period of variation of the resistance R with respect to the positive and negative of the alternating magnetic field Hac is ½ of the period of the alternating magnetic field Hac. In response to the signal magnetic field Hsig, an output voltage of an AC frequency component having the same period as that of the AC magnetic field Hac is generated.

The above characteristics are obtained when the signal magnetic field Hsig does not change with time. When the signal magnetic field Hsig changes with time, it becomes as follows. Let the frequency of the signal magnetic field Hsig be the signal frequency fsig. Let the frequency of the alternating magnetic field Hac be the alternating frequency fac. At this time, an output corresponding to the signal magnetic field Hsig is generated at a frequency of fac±fsig.

When the signal magnetic field Hsig changes with time, the signal frequency fsig is, for example, 1 kHz or less. On the other hand, the AC frequency fac is sufficiently higher than the signal frequency fsig. For example, the AC frequency fac is 10 times or more of the signal frequency fsig.

For example, the signal magnetic field Hsig can be detected with high accuracy by extracting the output voltage of a component (AC frequency component) having the same period (frequency) as the period (frequency) of the AC magnetic field Hac. In the magnetic sensor 110 according to the embodiment, the external magnetic field Hex (signal magnetic field Hsig) to be detected can be detected with high sensitivity by using such characteristics. In the embodiment, the external magnetic field Hex (signal magnetic field Hsig) and the alternating magnetic field Hac by the first current I1 can be efficiently applied to the first magnetic element 11. High sensitivity can be obtained.

One of the first magnetic layer 11a and the first opposing magnetic layer 11b may be a magnetization free layer. The other of the first magnetic layer 11a and the first opposing magnetic layer 11b may be a reference layer. By changing the angle between the magnetization of these magnetic layers, the electrical resistance changes.

Figure 7A:
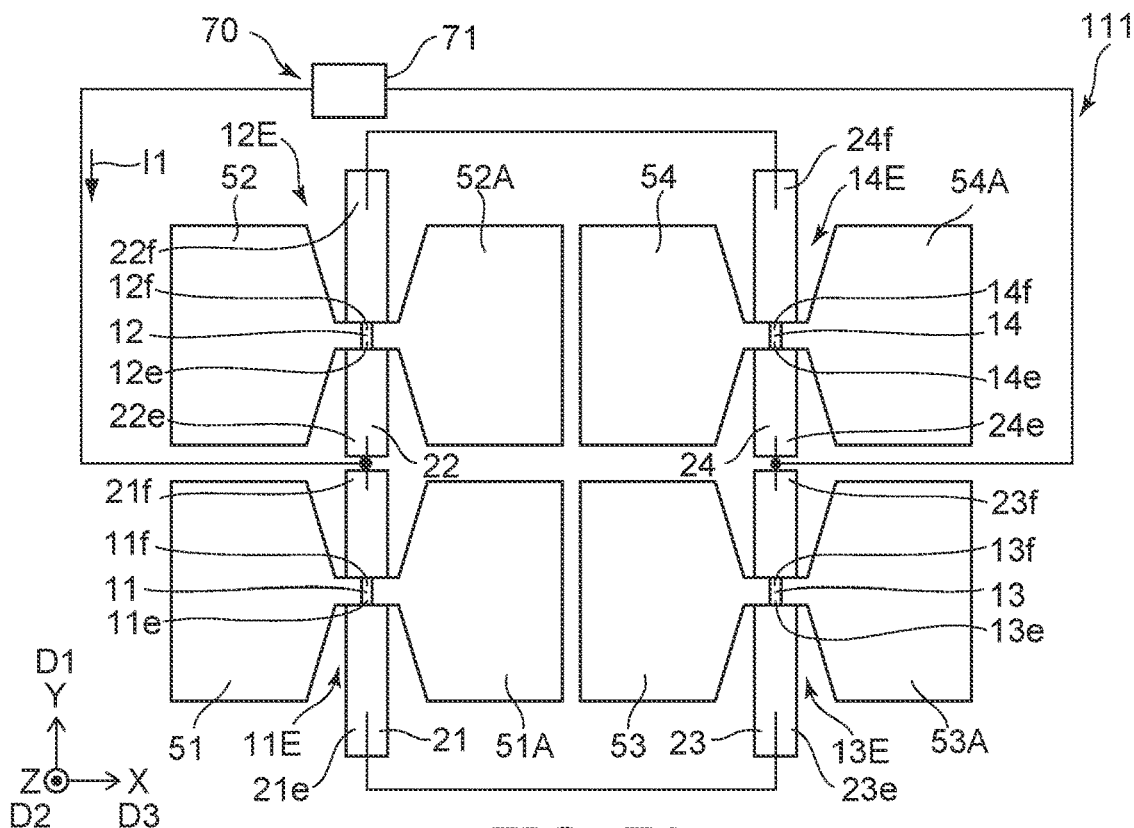
FIGS. 7A and 7B are schematic plan views illustrating the magnetic sensor according to the first embodiment.
Figure 7B:
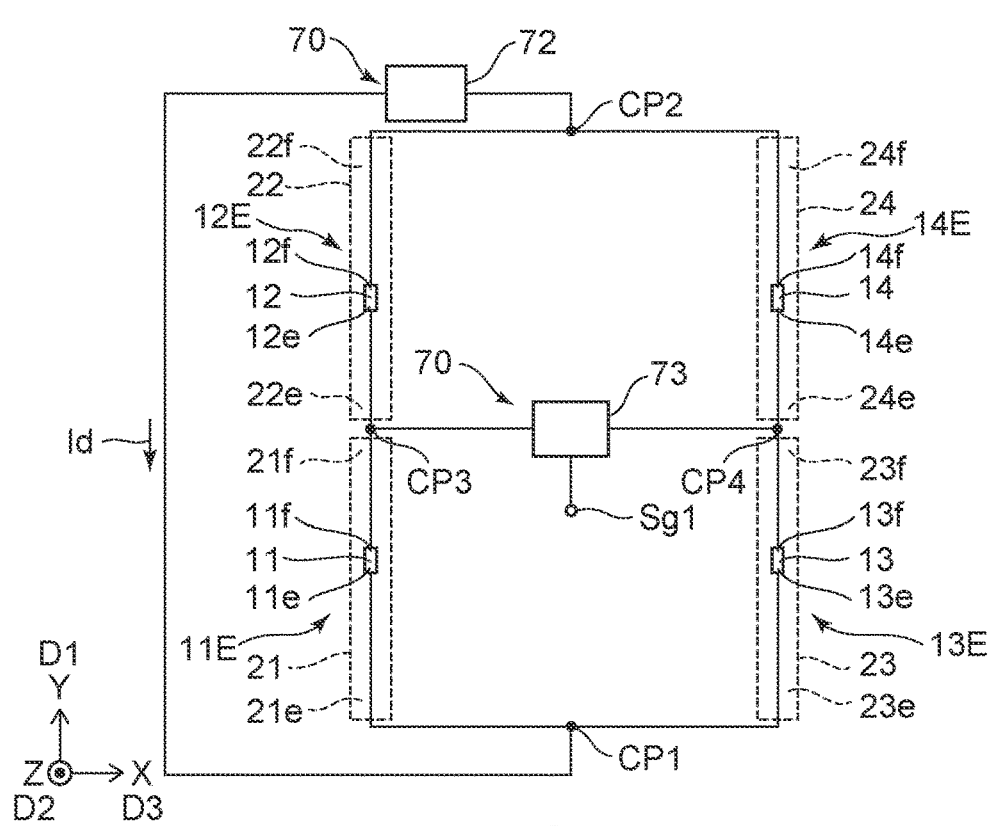

FIGS. 7A and 7B are schematic plan views illustrating the magnetic sensor according to the first embodiment.

Figure 8A:
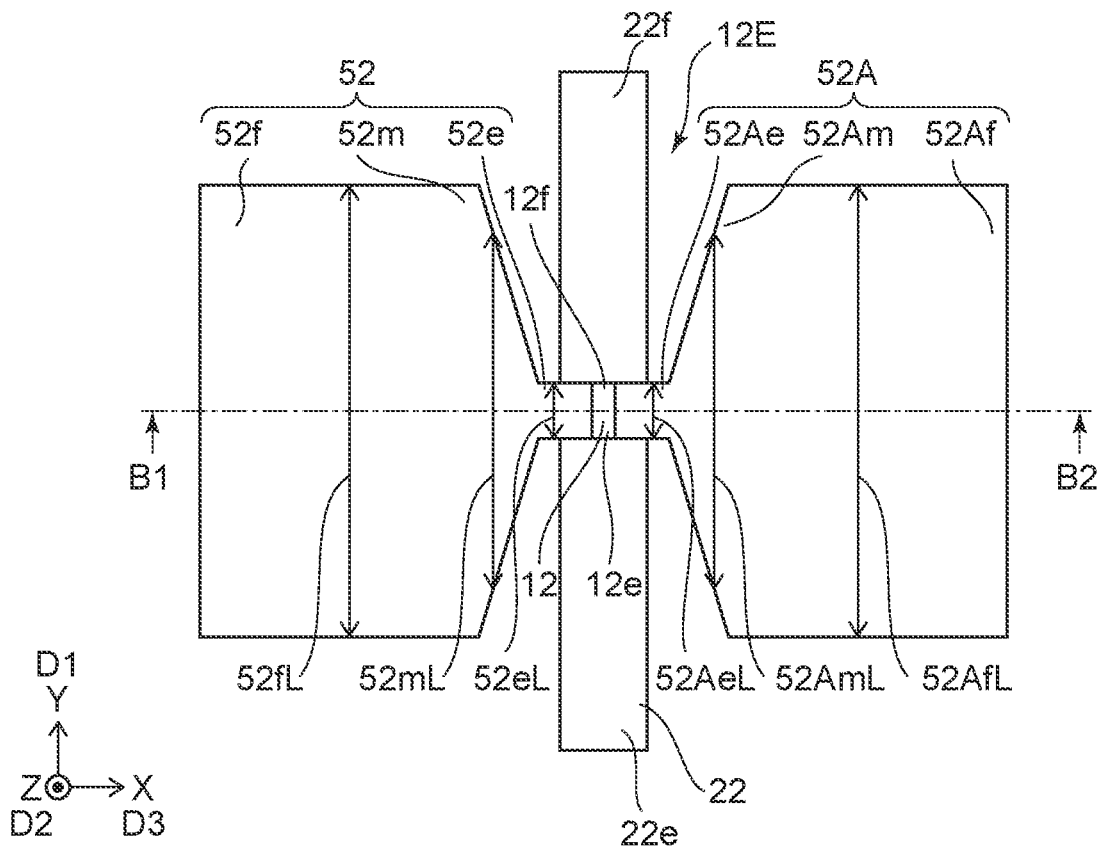
FIGS. 8A and 8B are schematic views illustrating a part of the magnetic sensor according to the first embodiment.
Figure 8B:
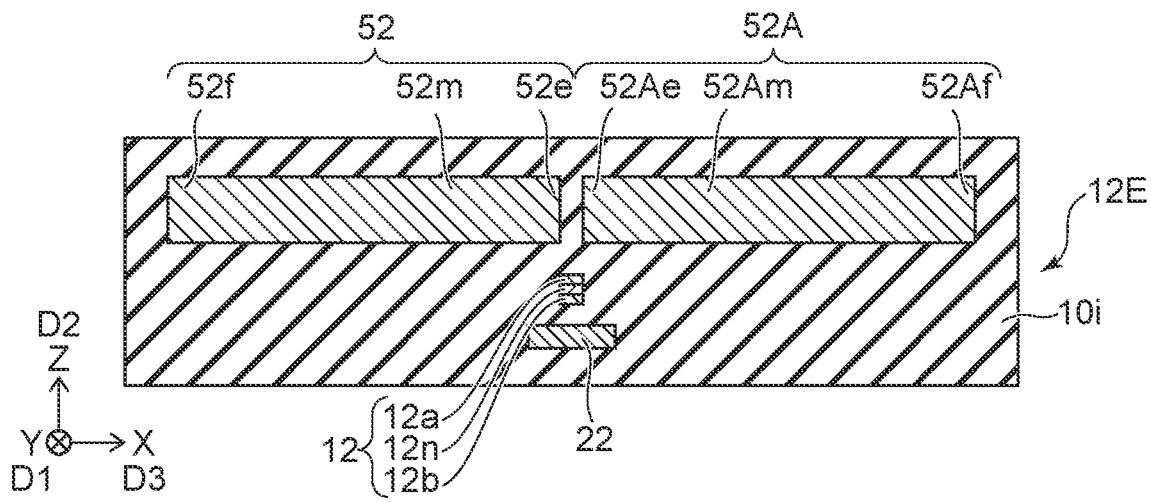

FIGS. 8A and 8B are schematic views illustrating a part of the magnetic sensor according to the first embodiment.

FIG. 8A is a plan view. FIG. 8B is a cross-sectional view taken along the line B1-B2 of FIG. 8A.

Figure 9A:
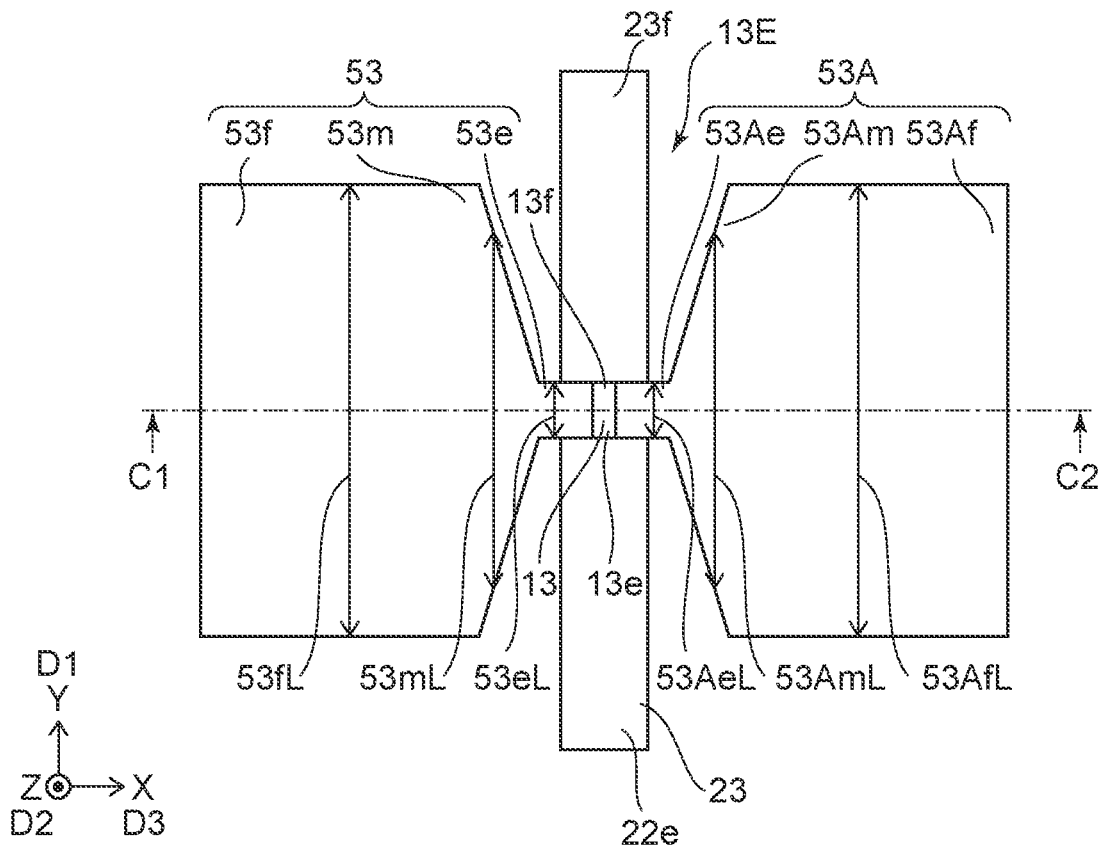
FIGS. 9A and 9B are schematic views illustrating a part of the magnetic sensor according to the first embodiment.
Figure 9B:
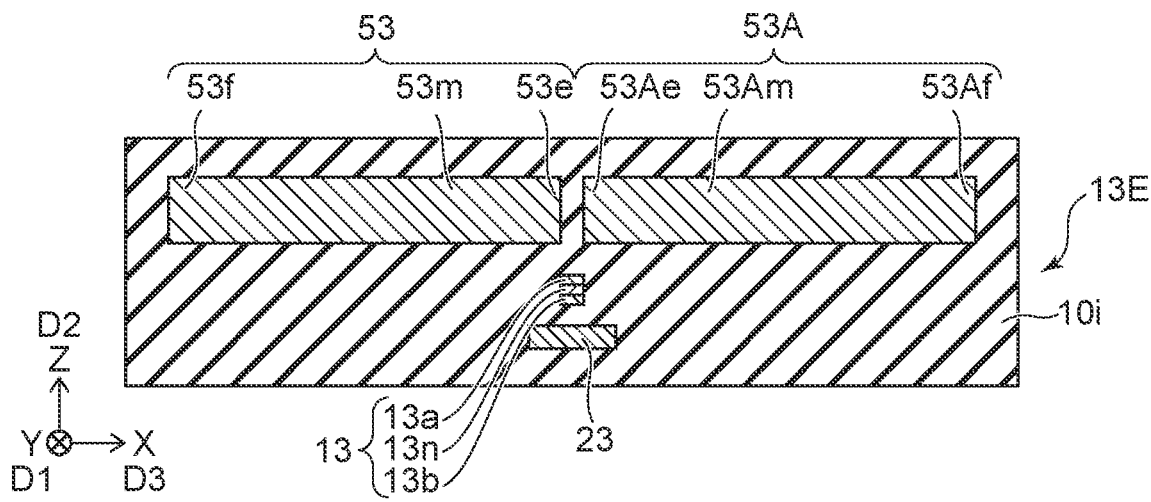

FIGS. 9A and 9B are schematic views illustrating a part of the magnetic sensor according to the first embodiment.

FIG. 9A is a plan view. FIG. 9B is a cross-sectional view taken along the line C1-C2 of FIG. 9A.

Figure 10A:
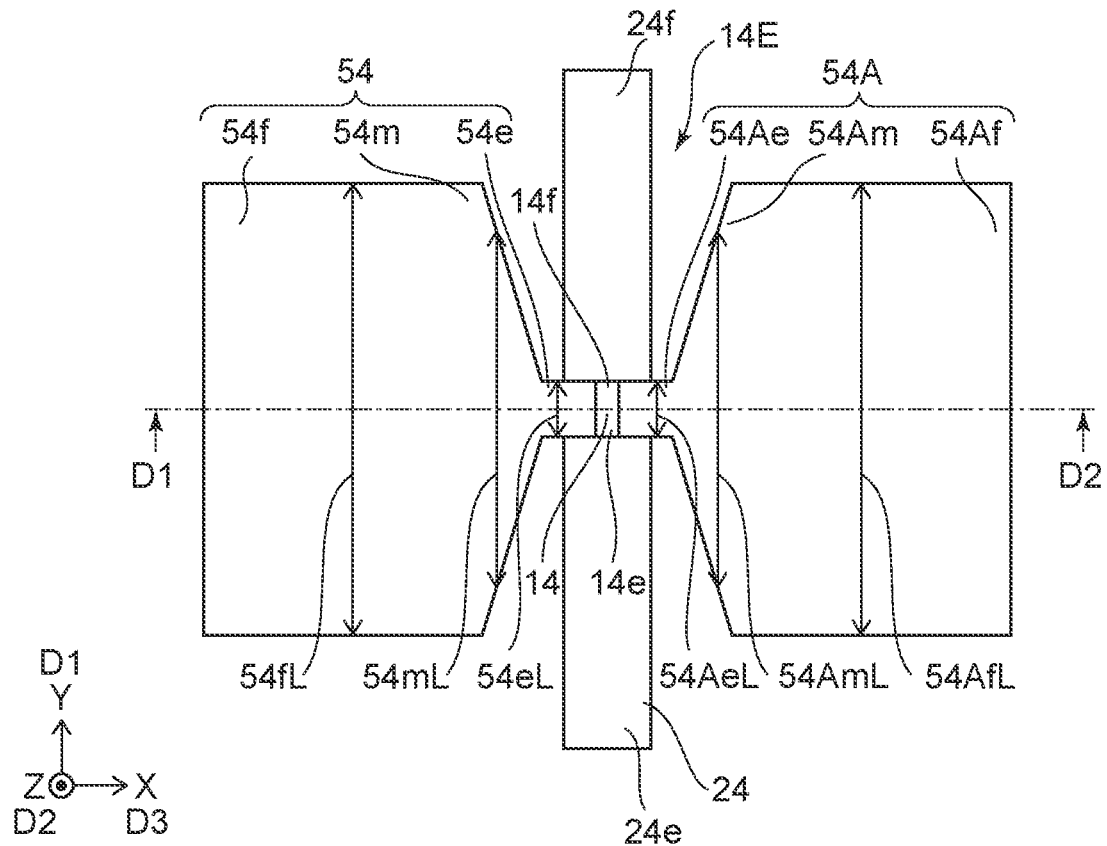
FIGS. 10A and 10B are schematic views illustrating a part of the magnetic sensor according to the first embodiment.
Figure 10B:
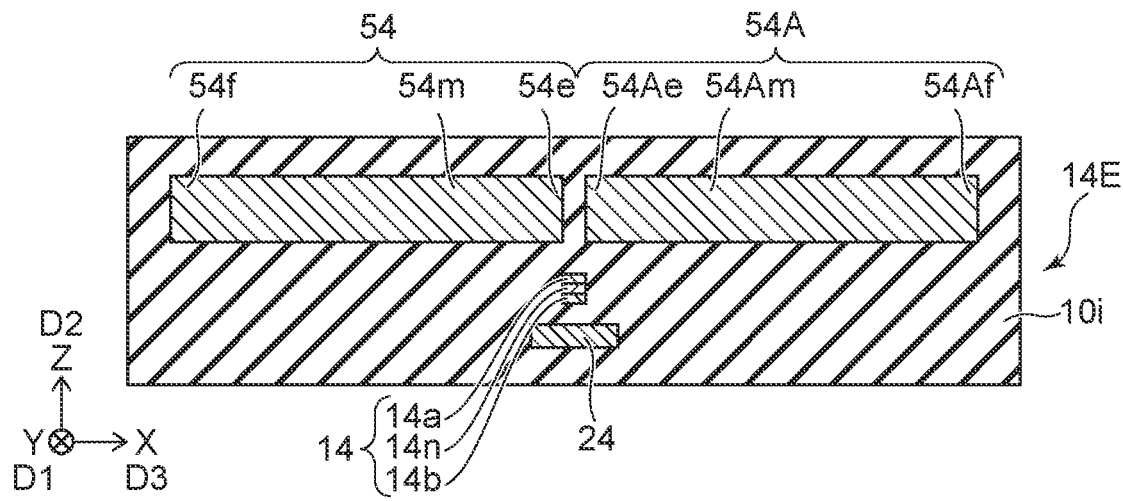

FIGS. 10A and 10B are schematic views illustrating a part of the magnetic sensor according to the first embodiment.

FIG. 10A is a plan view. FIG. 10B is a cross-sectional view taken along the line D1-D2 of FIG. 10A.

As shown in FIG. 7A, a magnetic sensor 111 according to the embodiment further includes a second element portion 12E. In this example, the magnetic sensor 111 further includes a third element portion 13E and a fourth element portion 14E.

The second element portion 12E includes a second magnetic element 12, a second conductive member 22, a second magnetic member 52, and a second opposing magnetic member 52A. The second magnetic element 12 includes a second end portion 12ed and a second other end portion 12f. A direction from the second end portion 12e to the second other end portion 12f is along the first direction D1.

As shown in FIG. 8B, a direction from the second conductive member 22 to the second magnetic element 12 is along the second direction D2. As shown in FIG. 8A, the second conductive member 22 includes a second conductive portion 22e and a second other conductive portion 22f. A direction from the second conductive portion 22e to the second other conductive portion 22f is along the first direction D1. A distance between the second conductive portion 22e and the second end portion 12e is shorter than a distance between the second conductive portion 22e and the second other end portion 12f. The distance between the second other conductive portion 22f and the second other end portion 12f is shorter than a distance between the second other conductive portion 22*f* and the second end portion 12*e*.

A direction from the second magnetic member 52 to the second opposing magnetic member 52A is along the third direction D3. A position of at least a part of the second magnetic element 12 in the third direction D3 is between a position of the second magnetic member 52 in the third direction D3 and the position of the second opposing magnetic member 52A in the third direction D3.

As shown in FIG. 7B, in this example, the first other end portion 11*f* is electrically connected to the second end portion 12*e*. The first other conductive portion 21*f* is electrically connected to the second conductive portion 22*e*. The first other conductive portion 21*f* may be continuous with the second conductive portion 22*e*. The boundary between the first other conductive portion 21*f* and the second conductive portion 22*e* may be unclear or clear. One portion of one conductive member may correspond to the first conductive member 21 and another portion may correspond to the second conductive member 22.

As shown in FIG. 9A, the third element portion 13E includes a third magnetic element 13, a third conductive member 23, a third magnetic member 53 and a third opposing magnetic member 53A. The third magnetic element 13 includes a third end portion 13*e* and a third other end portion 13*f*. A direction from the third end portion 13*e* to the third other end portion 13*f* is along the first direction D1.

As shown in FIG. 9B, a direction from the third conductive member 23 to the third magnetic element 13 is along the second direction D2.

As shown in FIG. 9A, the third conductive member 23 includes a third conductive portion 23*e* and a third other conductive portion 23*f*. A direction from the third conductive portion 23*e* to the third other conductive portion 23*f* is along the first direction D1. A distance between the third conductive portion 23*e* and the third end portion 13*e* is shorter than a distance between the third conductive portion 23*e* and the third other end portion 13*f*. A distance between the third other conductive portion 23*f* and the third other end portion 13*f* is shorter than a distance between the third other conductive portion 23*f* and the third end portion 13*e*.

As shown in FIGS. 9A and 9B, a direction from the third magnetic member 53 to the third opposing magnetic member 53A is along the third direction D3. A position of at least part of the third magnetic element 13 in the third direction D3 is between a position of the third magnetic member 53 in the third direction D3 and a position of the third opposing magnetic member 53A in the third direction D3.

As shown in FIG. 10A, the fourth element portion 14E includes a fourth magnetic element 14, a fourth conductive member 24, a fourth magnetic member 54 and a fourth opposing magnetic member 54A. The fourth magnetic element 14 includes a fourth end portion 14*e* and a fourth other end portion 14*f*. A direction from the fourth end portion 14*e* to the fourth other end portion 14*f* is along the first direction D1.

As shown in FIG. 10B, a direction from the fourth conductive member 24 to the fourth magnetic element 14 is along the second direction D2.

As shown in FIG. 10A, the fourth conductive member 24 includes a fourth conductive portion 24*e* and a fourth other conductive portion 24*f*. A direction from the fourth conductive portion 24*e* to the fourth other conductive portion 24*f* is along the first direction D1. A distance between the fourth conductive portion 24*e* and the fourth end portion 14*e* is shorter than a distance between the fourth conductive portion 24*e* and the fourth other end portion 14*f*. A distance between the fourth other conductive portion 24*f* and the fourth other end portion 14*f* is shorter than a distance between the fourth other conductive portion 24*f* and the fourth end portion 14*e*.

As shown in FIGS. 10A and 10B, a direction from the fourth magnetic member 54 to the fourth opposing magnetic member 54A is along the third direction D3. A position of at least part of the fourth magnetic element 14 in the third direction D3 is between a position of the fourth magnetic member 54 in the third direction D3 and a position of the fourth opposing magnetic member 54A in the third direction D3.

As shown in FIG. 7B, in this example, the second other end portion 12*f* is electrically connected to the fourth other end portion 14*f*. The third end portion 13*e* is electrically connected to the first end portion 11*e*. The third other end portion 13*f* is electrically connected to the fourth end portion 14*e*. The second other conductive portion 22*f* is electrically connected to the fourth other conductive portion 24*f*. The third conductive portion 23*e* is electrically connected to the first conductive portion 21*e*. The third other conductive portion 23*f* is electrically connected to the fourth conductive portion 24*e*.

The third other conductive portion 23*f* may be continuous with the fourth conductive portion 24*e*. The boundary between the third other conductive portion 23*f* and the fourth conductive portion 24*e* may be unclear or clear. One portion of one conductive member may correspond to the third conductive member 23 and another portion may correspond to the fourth conductive member 24.

As shown in FIGS. 7A and 7B, the magnetic sensor 111 may include a circuit portion. The circuit portion 70 includes the first circuit 71, the second circuit 72 and the third circuit 73. The first circuit 71 can supply a first current I1 including an AC component between the first other conductive portion 21*f* and the third other conductive portion 23*f*.

The second circuit 72 can supply the element current Id or the element voltage between a first connection point CP1 of the first end portion 11*e* and the third end portion 13*e* and a second connection point CP2 of the second other end portion 12*f* and the fourth other end portion 14*f*.

The third circuit 73 can output the signal Sg1 corresponding to an electric signal generated between the third connection point CP3 of the first other end portion 11*f* and the second end portion 12*e* and the fourth connection point CP4 of the third other end portion 13*f* and the fourth end portion 14*e*. By applying the bridge circuit, detection with more suppressed noise is possible.

As shown in FIG. 8A, the second magnetic member 52 includes a second other magnetic portion 52*f* and a second magnetic portion 52*e*. A direction from the second magnetic portion 52*e* to the second magnetic portion 52*e* is along the third direction D3. A second other magnetic partial length 52*f*L along the first direction D1 of the second other magnetic portion 52*f* is longer than a second magnetic partial length 52*e*L along the first direction D1 of the second magnetic portion 52*e*. The second conductive member 22 overlaps the second magnetic portion 52*e* in the second direction D2. The second conductive member 22 does not overlap the second other magnetic portion 52*f* in the second direction D2.

As shown in FIG. 8A, the second magnetic member 52 may further include a second intermediate magnetic portion 52*m*. The second intermediate magnetic portion 52*m* is located between the second other magnetic portion 52*f* and the second magnetic portion 52*e* in the third direction D3. A length of the second intermediate magnetic portion 52*m* along the first direction D1 is defined as a second intermediate magnetic portion length 52mL. The second intermediate magnetic portion length 52mL is between the second magnetic other portion length 52fL and the second magnetic portion length 52eL.

The rate of change in the third direction D3 of the second magnetic portion length 52eL is lower than the rate of change in the third direction D3 of the second intermediate magnetic portion length 52mL. The second conductive member 22 does not overlap the second intermediate magnetic portion 52m in the second direction D2. Thereby, noise can be suppressed. The rate of change in the third direction D3 of the second other magnetic portion length 52fL is lower than the rate of change in the third direction D3 of the second intermediate magnetic portion length 52mL.

As shown in FIG. 9A, for example, the third magnetic member 53 includes a third other magnetic portion 53f and a third magnetic portion 53e. A direction from the third other magnetic portion 53f to the third magnetic portion 53e is along the third direction D3. A third other magnetic portion length 53fL along the first direction D1 of the third other magnetic portion 53f is longer than a third magnetic portion length 53eL along the first direction D1 of the third magnetic portion 53e. The third conductive member 23 overlaps the third magnetic portion 53e in the second direction D2. The third conductive member 23 does not overlap the third other magnetic portion 53f in the second direction D2.

As shown in FIG. 10A, the fourth magnetic member 54 includes a fourth other magnetic portion 54f and a fourth magnetic portion 54e. A direction from the fourth other magnetic portion 54f to the fourth magnetic portion 54e is along the third direction D3. A fourth other magnetic portion length 54fL along the first direction D1 of the fourth other magnetic portion 54f is longer than a fourth magnetic portion length 54eL along the first direction D1 of the fourth magnetic portion 54e. The fourth conductive member 24 overlaps the fourth magnetic portion 54e in the second direction D2. The fourth conductive member 24 does not overlap the fourth other magnetic portion 54f in the second direction D2.

As shown in FIG. 9A, the third magnetic member 53 may further include a third intermediate magnetic portion 53m. The third intermediate magnetic portion 53m is between the third other magnetic portion 53f and the third magnetic portion 53e in the third direction D3. A length of the third intermediate magnetic portion 53m along the first direction D1 is defined as a third intermediate magnetic portion length 53mL. The third intermediate magnetic portion length 53mL is between the third other magnetic portion length 53fL and the third magnetic portion length 53eL.

The rate of change in the third direction D3 of the third magnetic portion length 53eL is lower than the rate of change in the third direction D3 of the third intermediate magnetic portion length 53mL. The third conductive member 23 does not overlap the third intermediate magnetic portion 53m in the second direction D2. Thereby, noise can be suppressed. The rate of change in the third direction D3 of the third other magnetic portion length 53fL is lower than the rate of change in the third direction D3 of the third intermediate magnetic portion length 53mL.

As shown in FIG. 10A, the fourth magnetic member 54 may further include a fourth intermediate magnetic portion 54m. The fourth intermediate magnetic portion 54m is between the fourth other magnetic portion 54f and the fourth magnetic portion 54e in the third direction D3. A length of the fourth intermediate magnetic portion 54m along the first direction D1 is defined as a fourth intermediate magnetic portion length 54mL. The fourth intermediate magnetic portion length 54mL is between the fourth other magnetic portion length 54fL and the fourth magnetic portion length 54eL.

The rate of change in the third direction D3 of the fourth magnetic portion length 54eL is lower than the rate of change in the third direction D3 of the fourth intermediate magnetic portion length 54mL. The fourth conductive member 24 does not overlap the fourth intermediate magnetic portion 54m in the second direction D2. Thereby, noise can be suppressed. The change rate in the third direction D3 of the fourth other magnetic portion length 54fL is lower than the change rate in the third direction D3 of the fourth intermediate magnetic portion length 54mL.

As shown in FIG. 8A, the second opposing magnetic member 52A includes a second opposing other magnetic portion 52Af and a second opposing magnetic portion 52Ae. A direction from the second opposing magnetic portion 52Ae to the second opposing other magnetic portion 52Af is along the third direction D3. The length (width) of the second opposing other magnetic portion 52Af in the first direction D1 is defined as a second opposing other magnetic portion length 52AfL. The length (width) of the second opposing magnetic portion 52Ae in the first direction D1 is defined as a second opposing magnetic portion length 52AeL. The second opposing magnetic portion length 52AfL is longer than the second opposing magnetic portion length 52AeL.

As shown in FIGS. 8A and 8B, the second conductive member 22 overlaps the second opposing magnetic portion 52Ae in the second direction D2. The second conductive member 22 does not overlap the second opposing other magnetic portion 52Af in the second direction D2.

As shown in FIG. 8A, the second opposing magnetic member 52A may further include a second opposing intermediate magnetic portion 52Am. The second opposing intermediate magnetic portion 52Am is between the second opposing other magnetic portion 52Af and the second opposing magnetic portion 52Ae in the third direction D3. A length of the second opposing intermediate magnetic portion 52Am along the first direction D1 is defined as a second opposing intermediate magnetic portion length 52AmL. The second opposing intermediate magnetic portion length 52AmL is between the second opposing other magnetic portion length 52AfL and the second opposing magnetic portion length 52AeL.

The rate of change in the third direction D3 of the second opposing magnetic portion length 52AeL is lower than the rate of change in the third direction D3 of the second opposing intermediate magnetic portion length 52AmL. The second conductive member 22 does not overlap the second opposing intermediate magnetic portion 52Am in the second direction D2. Thereby, noise can be suppressed.

As shown in FIG. 9A, the third opposing magnetic member 53A includes a third opposing other magnetic portion 53Af and a third opposing magnetic portion 53Ae. A direction from the third opposing magnetic portion 53Ae to the third opposing other magnetic portion 53Af is along the third direction D3. A length (width) of the third opposing other magnetic portion 53Af in the first direction D1 is defined as a third opposing magnetic portion length 53AfL. A length (width) of the third opposing magnetic portion 53Ae in the first direction D1 is defined as a third opposing magnetic portion length 53AeL. The third opposing magnetic portion length 53AfL is longer than the third opposing magnetic portion length 53AeL.

As shown in FIGS. 9A and 9B, the third conductive member 23 overlaps the third opposing magnetic portion 53Ae in the second direction D2. The third conductive member 23 does not overlap the third opposing other magnetic portion 53Af in the second direction D2.

As shown in FIG. 9A, the third opposing magnetic member 53A may further include a third opposing intermediate magnetic portion 53Am. The third opposing intermediate magnetic portion 53Am is between the third opposing other magnetic portion 53Af and the third opposing magnetic portion 53Ae in the third direction D3. A length of the third opposing intermediate magnetic portion 53Am along the first direction D1 is defined as a third opposing intermediate magnetic portion length 53AmL. The third opposing intermediate magnetic portion length 53AmL is between the third opposing other magnetic portion length 53AfL and the third opposing magnetic portion length 53AeL.

The rate of change in the third direction D3 of the third opposing magnetic portion length 53AeL is lower than the rate of change in the third direction D3 of the third opposing intermediate magnetic portion length 53AmL. The third conductive member 23 does not overlap the third opposing intermediate magnetic portion 53Am in the second direction D2. Thereby, noise can be suppressed.

As shown in FIG. 10A, the fourth opposing magnetic member 54A includes a fourth opposing other magnetic portion 54Af and a fourth opposing magnetic portion 54Ae. A direction from the fourth opposing magnetic portion 54Ae to the fourth opposing other magnetic portion 54Af is along the third direction D3. A length (width) of the fourth opposing other magnetic portion 54Af in the first direction D1 is defined as a fourth opposing other magnetic portion length 54AfL. A length (width) of the fourth opposing magnetic portion 54Ae in the first direction D1 is defined as a fourth opposing magnetic portion length 54AeL. The fourth opposing other magnetic portion length 54AfL is longer than the fourth opposing magnetic portion length 54AeL.

As shown in FIGS. 10A and 10B, the fourth conductive member 24 overlaps the fourth opposing magnetic portion 54Ae in the second direction D2. The fourth conductive member 24 does not overlap the fourth opposing other magnetic portion 54Af in the second direction D2.

As shown in FIG. 10A, the fourth opposing magnetic member 54A may further include a fourth opposing intermediate magnetic portion 54Am. The fourth opposing intermediate magnetic portion 54Am is between the fourth opposing other magnetic portion 54Af and the fourth opposing magnetic portion 54Ae in the third direction D3. A length of the fourth opposing intermediate magnetic portion 54Am along the first direction D1 is defined as a fourth opposing intermediate magnetic portion length 54AmL. The fourth opposing intermediate magnetic portion length 54AmL is between the fourth opposing other magnetic portion length 54AfL and the fourth opposing magnetic portion length 54AeL.

The change rate in the third direction D3 of the fourth opposing magnetic portion length 54AeL is lower than the change rate in the third direction D3 of the fourth opposing intermediate magnetic portion length 54AmL. The fourth conductive member 24 does not overlap the fourth opposing intermediate magnetic portion 54Am in the second direction D2. Thereby, noise can be suppressed.

As shown in FIG. 8B, the second magnetic element 12 includes, for example, a second magnetic layer 12a, a second opposing magnetic layer 12b and a second non-magnetic layer 12n. A direction from the second opposing magnetic layer 12b to the second magnetic layer 12a is along the second direction D2. The second non-magnetic layer 12n is between the second opposing magnetic layer 12b and the second magnetic layer 12a.

As shown in FIG. 9B, the third magnetic element 13 includes, for example, a third magnetic layer 13a, a third opposing magnetic layer 13b and a third non-magnetic layer 13n. A direction from the third opposing magnetic layer 13b to the third magnetic layer 13a is along the second direction D2. The third non-magnetic layer 13n is between the third opposing magnetic layer 13b and the third magnetic layer 13a.

As shown in FIG. 10B, the fourth magnetic element 14 includes, for example, a fourth magnetic layer 14a, a fourth opposing magnetic layer 14b and a fourth non-magnetic layer 14n. A direction from the fourth opposing magnetic layer 14b to the fourth magnetic layer 14a is along the second direction D2. The fourth non-magnetic layer 14n is between the fourth opposing magnetic layer 14b and the fourth magnetic layer 14a.

At least one of the second magnetic layer 12a, the third magnetic layer 13a, and the fourth magnetic layer 14a may include the material included in the first magnetic layer 11a. At least one of the second opposing magnetic layer 12b, the third opposing magnetic layer 13b, and the fourth opposing magnetic layer 14b may include the material included in the first opposing magnetic layer 11b. At least one of the second non-magnetic layer 12n, the third non-magnetic layer 13n, and the fourth non-magnetic layer 14n may include the material included in the first non-magnetic layer 11n.

Figure 11A:
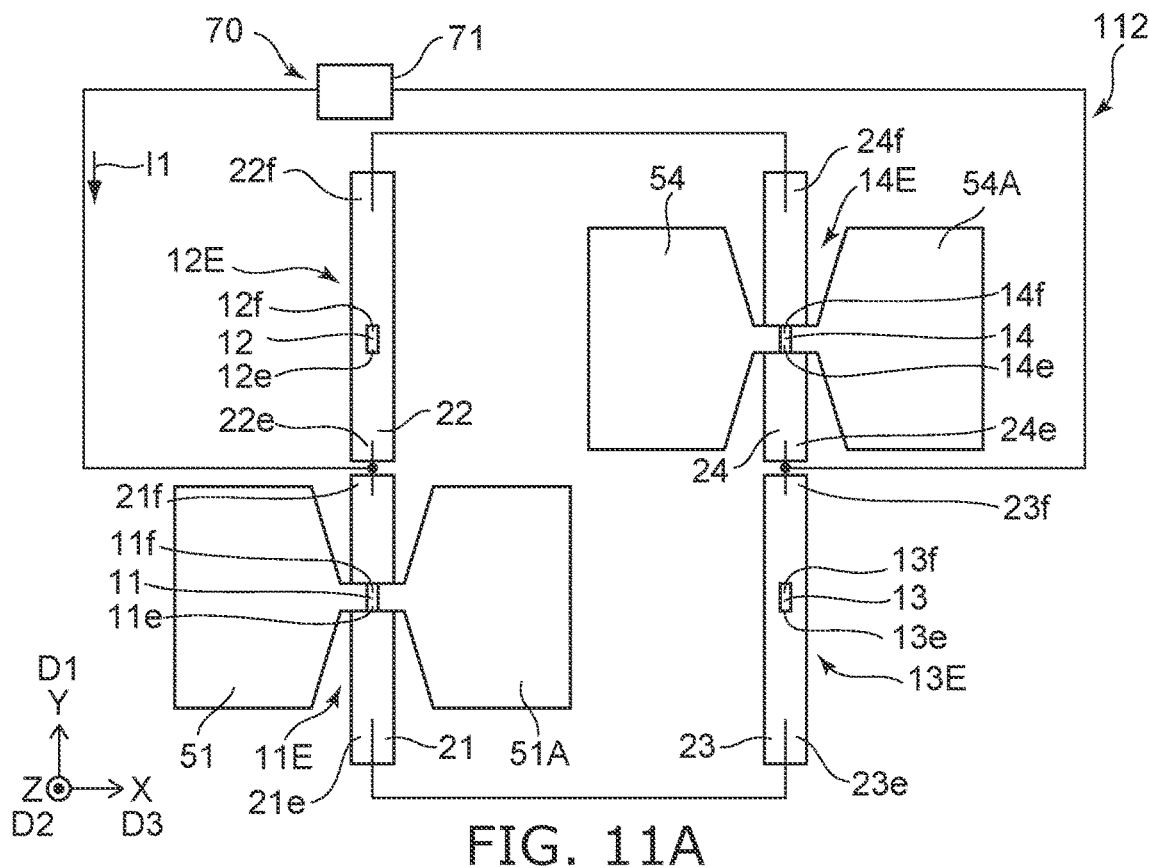
FIGS. 11A and 11B are schematic plan views illustrating the magnetic sensor according to the first embodiment.
Figure 11B:
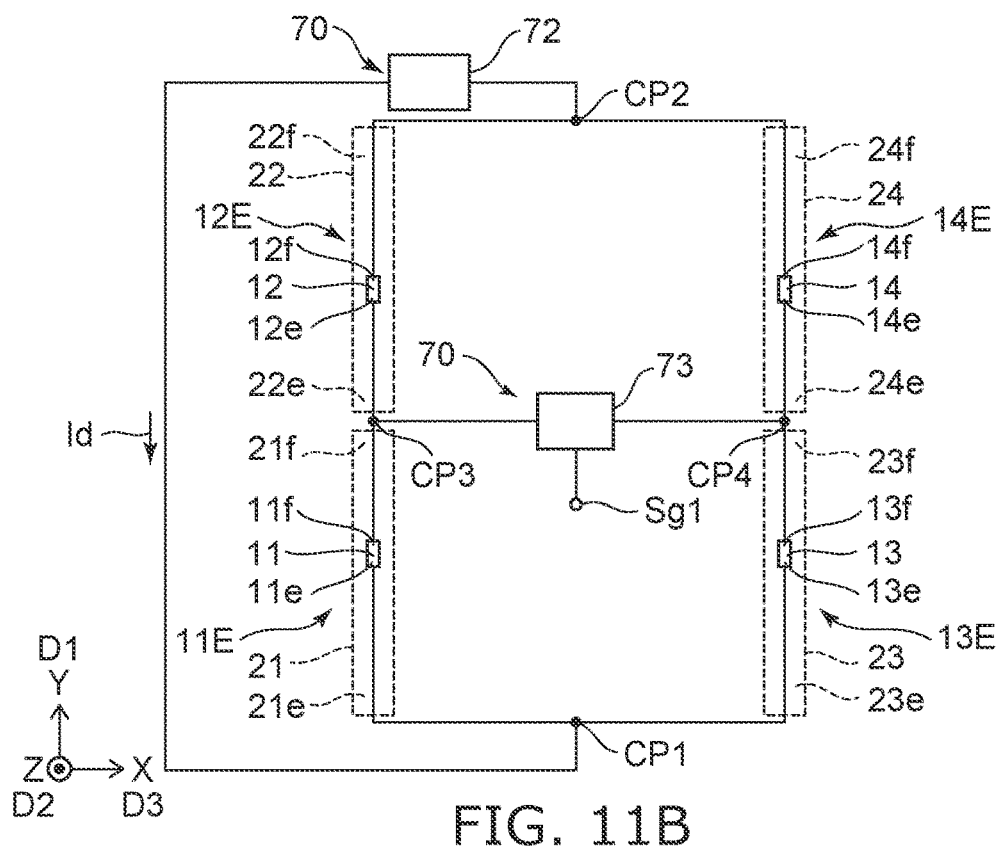

FIGS. 11A and 11B are schematic plan views illustrating the magnetic sensor according to the first embodiment.

As shown in FIG. 11A, in a magnetic sensor 112 according to the embodiment, the second magnetic member 52 and the second opposing magnetic member 52A may be omitted in the second element portion 12E. In the third element portion 13E, the third magnetic member 53 and the third opposing magnetic member 53A may be omitted. The configuration of the magnetic sensor 112 except for the above may be the same as that of the magnetic sensor 111. In the magnetic sensor 112, high sensitivity can be obtained while suppressing noise.

The magnetic sensor 112 includes a first element portion 11E, the second element portion 12E, the third element portion 13E and the fourth element portion 14E. The first element portion 11E in the magnetic sensor 112 may be the same as the first element portion 11E in the magnetic sensor 110.

The second element portion 12E includes the second magnetic element 12 and the second conductive member 22. The second magnetic element 12 includes the second end portion 12e and the second other end portion 12f. The direction from the second end portion 12e to the second other end portion 12f is along the first direction D1.

The direction from the second conductive member 22 to the second magnetic element 12 is along the second direction D2. The second conductive member 22 includes the second conductive portion 22e and the second other conductive portion 22f. The direction from the second conductive portion 22e to the second other conductive portion 22f is along the first direction D1. The distance between the second conductive portion 22e and the second end portion 12e is shorter than the distance between the second conductive portion 22e and the second other end portion 12f. The distance between the second other conductive portion 22f and the second other end portion 12f is shorter than the distance between the second other conductive portion 22f and the second end portion 12e.

The third element portion 13E includes the third magnetic element 13 and the third conductive member 23. The third magnetic element 13 includes the third end portion 13e and the third other end portion 13f. The direction from the third end portion 13e to the third other end portion 13f is along the first direction D1.

The direction from the third conductive member 23 to the third magnetic element 13 is along the second direction D2. The third conductive member 23 includes the third conductive portion 23e and the third other conductive portion 23f. The direction from the third conductive portion 23e to the third other conductive portion 23f is along the first direction D1. The distance between the third conductive portion 23e and the third end portion 13e is shorter than the distance between the third conductive portion 23e and the third other end portion 13f. The distance between the third other conductive portion 23f and the third other end portion 13f is shorter than the distance between the third other conductive portion 23f and the third end portion 13e.

The fourth element portion 14E includes the fourth magnetic element 14, the fourth conductive member 24, the fourth magnetic member 54 and the fourth opposing magnetic member 54A. The fourth magnetic element 14 includes the fourth end portion 14e and the fourth other end portion 14f. The direction from the fourth end portion 14e to the fourth other end portion 14f is along the first direction D1.

The direction from the fourth conductive member 24 to the fourth magnetic element 14 is along the second direction D2. The fourth conductive member 24 includes a fourth conductive portion 24e and a fourth other conductive portion 24f. The direction from the fourth conductive portion 24e to the fourth other conductive portion 24f is along the first direction D1. The distance between the fourth conductive portion 24e and the fourth end portion 14e is shorter than the distance between the fourth conductive portion 24e and the fourth other end portion 14f. The distance between the fourth other conductive portion 24f and the fourth other end portion 14f is shorter than the distance between the fourth other conductive portion 24f and the fourth end portion 14e.

The position of at least part of the fourth magnetic element 14 in the third direction D3 is between the position of the fourth magnetic member 54 in the third direction D3 and the position of the fourth opposing magnetic member 54A in the third direction D3.

The first other end portion 11f is electrically connected to the second end portion 12e. The second other end portion 12f is electrically connected to the fourth other end portion 14f. The third end portion 13e is electrically connected to the first end portion 11e. The third other end portion 13f is electrically connected to the fourth end portion 14e.

The first other conductive portion 21f is electrically connected to the second conductive portion 22e. The second other conductive portion 22f is electrically connected to the fourth other conductive portion 24f. The third conductive portion 23e is electrically connected to the first conductive portion 21e. The third other conductive portion 23f is electrically connected to the fourth conductive portion 24e.

The first circuit 71 can supply the first current I1 including an AC component between the first other conductive portion 21f and the third other conductive portion 23f.

The second circuit 72 can supply the element current Id or the element voltage between the first connection point CP1 of the first end portion 11e and the third end portion 13e and the second connection point CP2 of the second other end portion 12f and the fourth other end portion 14f.

The third circuit 73 can output the signal Sg1 corresponding to the electrical signal generated between the third connection point CP3 of the first other end portion 11f and the second end portion 12e and the fourth connection point CP4 of the third other end portion 13f and the fourth end portion 14e.

Figure 12:
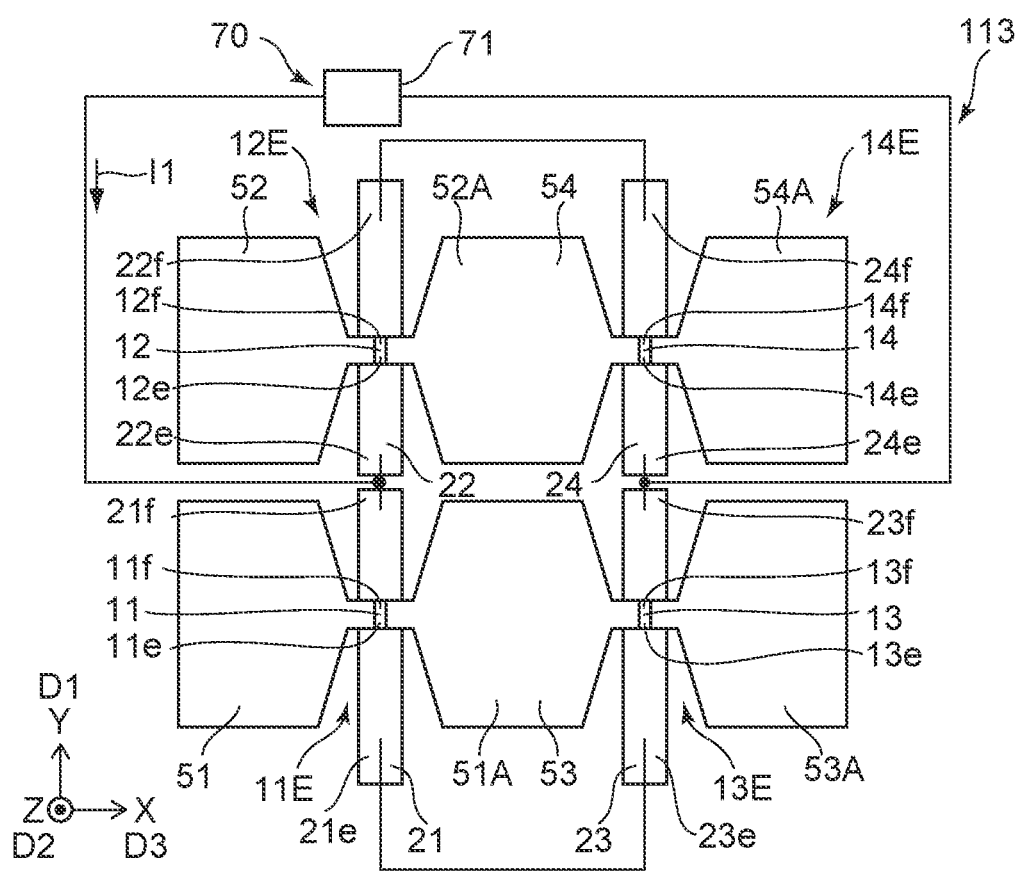
FIG. 12 is a schematic plan view illustrating the magnetic sensor according to the first embodiment.

FIG. 12 is a schematic plan view illustrating the magnetic sensor according to the first embodiment.

As shown in FIG. 12, in a magnetic sensor 113 according to the embodiment, the third magnetic member 53 is continuous with the first opposing magnetic member 51A. The fourth magnetic member 54 is continuous with the second opposing magnetic member 52A. The configuration of the magnetic sensor 113 excluding the above may be the same as the configuration of the magnetic sensor 111. Also in the magnetic sensor 113, high sensitivity can be obtained while suppressing noise.

Figure 13:
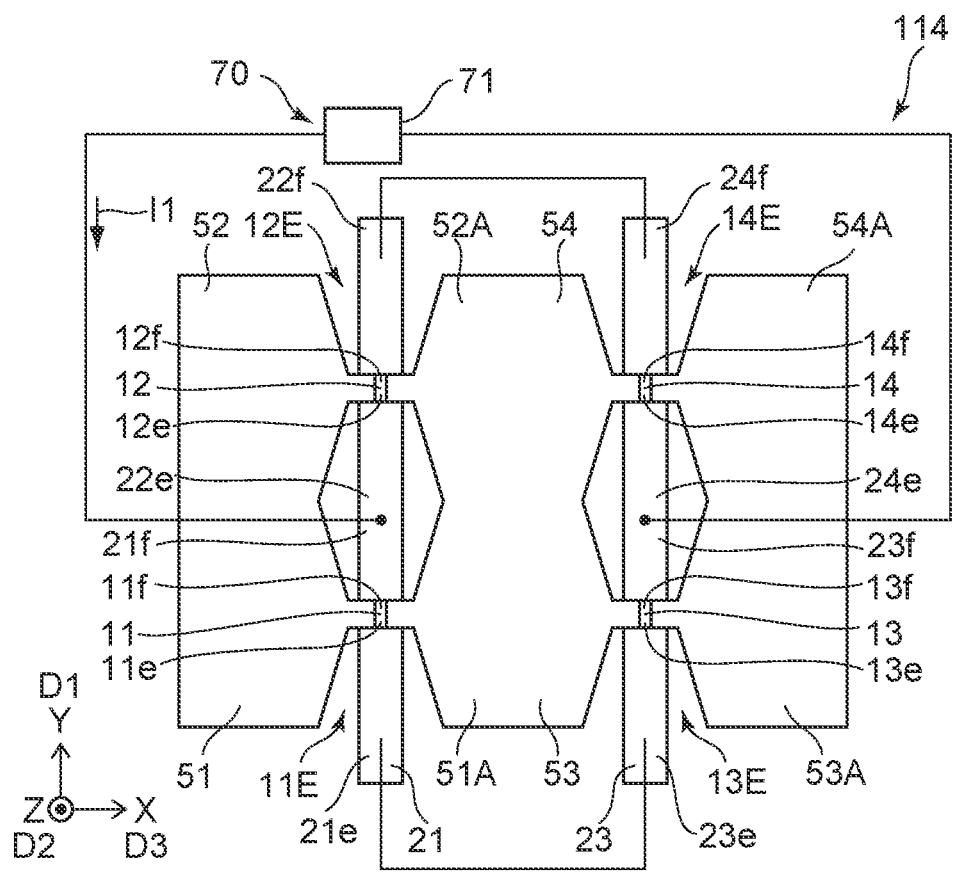
FIG. 13 is a schematic plan view illustrating the magnetic sensor according to the first embodiment.

FIG. 13 is a schematic plan view illustrating the magnetic sensor according to the first embodiment.

As shown in FIG. 13, in a magnetic sensor 114 according to the embodiment, the second magnetic member 52 is continuous with the first magnetic member 51. The second opposing magnetic member 52A is continuous with the first opposing magnetic member 51A. The fourth magnetic member 54 may be continuous with the third magnetic member 53. The fourth opposing magnetic member 54A is continuous with the third opposing magnetic member 53A. The configuration of the magnetic sensor 114 excluding the above may be the same as the configuration of the magnetic sensor 113. Also in the magnetic sensor 114, high sensitivity can be obtained while suppressing noise.

Figure 14:
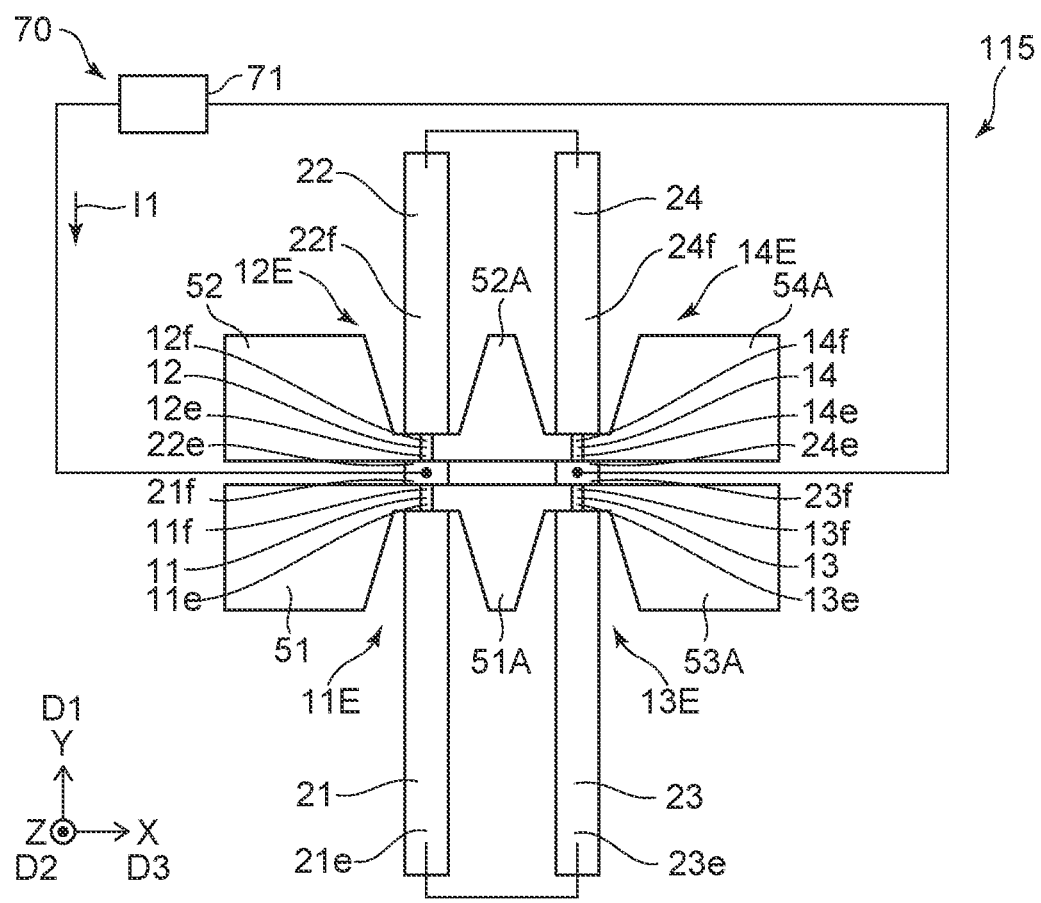
FIG. 14 is a schematic plan view illustrating the magnetic sensor according to the first embodiment.

FIG. 14 is a schematic plan view illustrating the magnetic sensor according to the first embodiment.

As shown in FIG. 14, in a magnetic sensor 115 according to the embodiment, each of the first magnetic member 51, the first opposing magnetic member 51A, the second magnetic member 52, the second opposing magnetic member 52A, the third magnetic member 53, the third opposing magnetic member 53A, the fourth magnetic member 54, and the fourth opposing magnetic member 54A may be asymmetric with respect to a line along the X-axis direction. The configuration of the magnetic sensor 115 excluding the above may be the same as the configuration of the magnetic sensor 113. Also in the magnetic sensor 115, high sensitivity can be obtained while suppressing noise.

Figure 15:
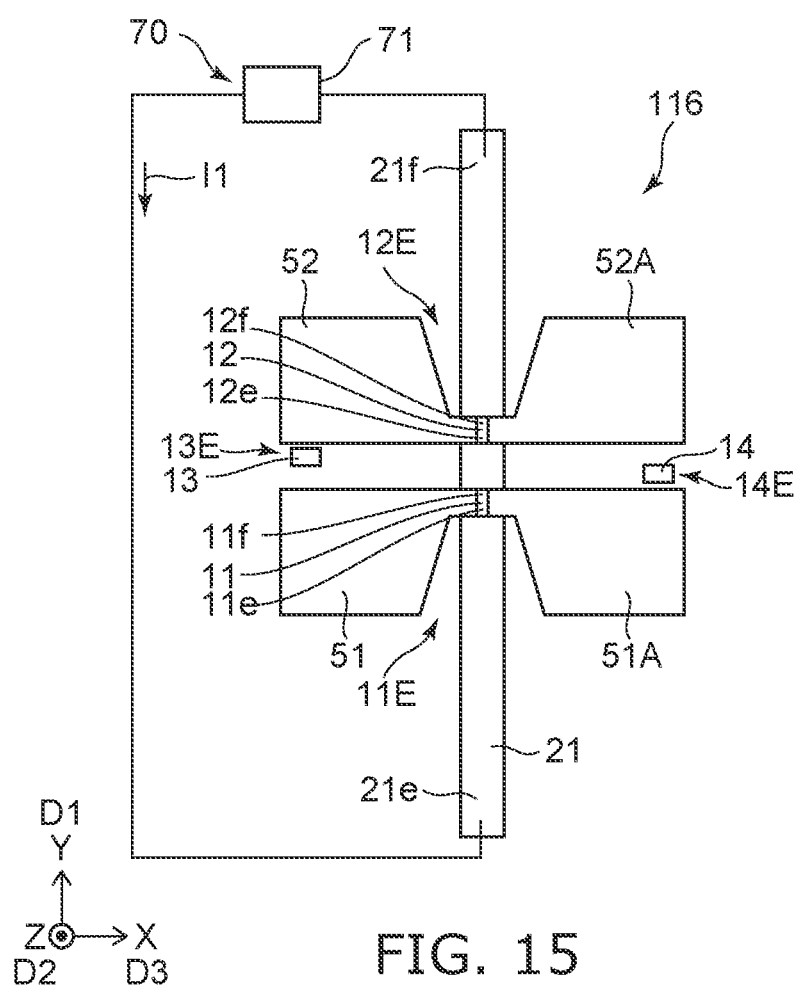
FIG. 15 is a schematic plan view illustrating the magnetic sensor according to the first embodiment.
Figure 16:
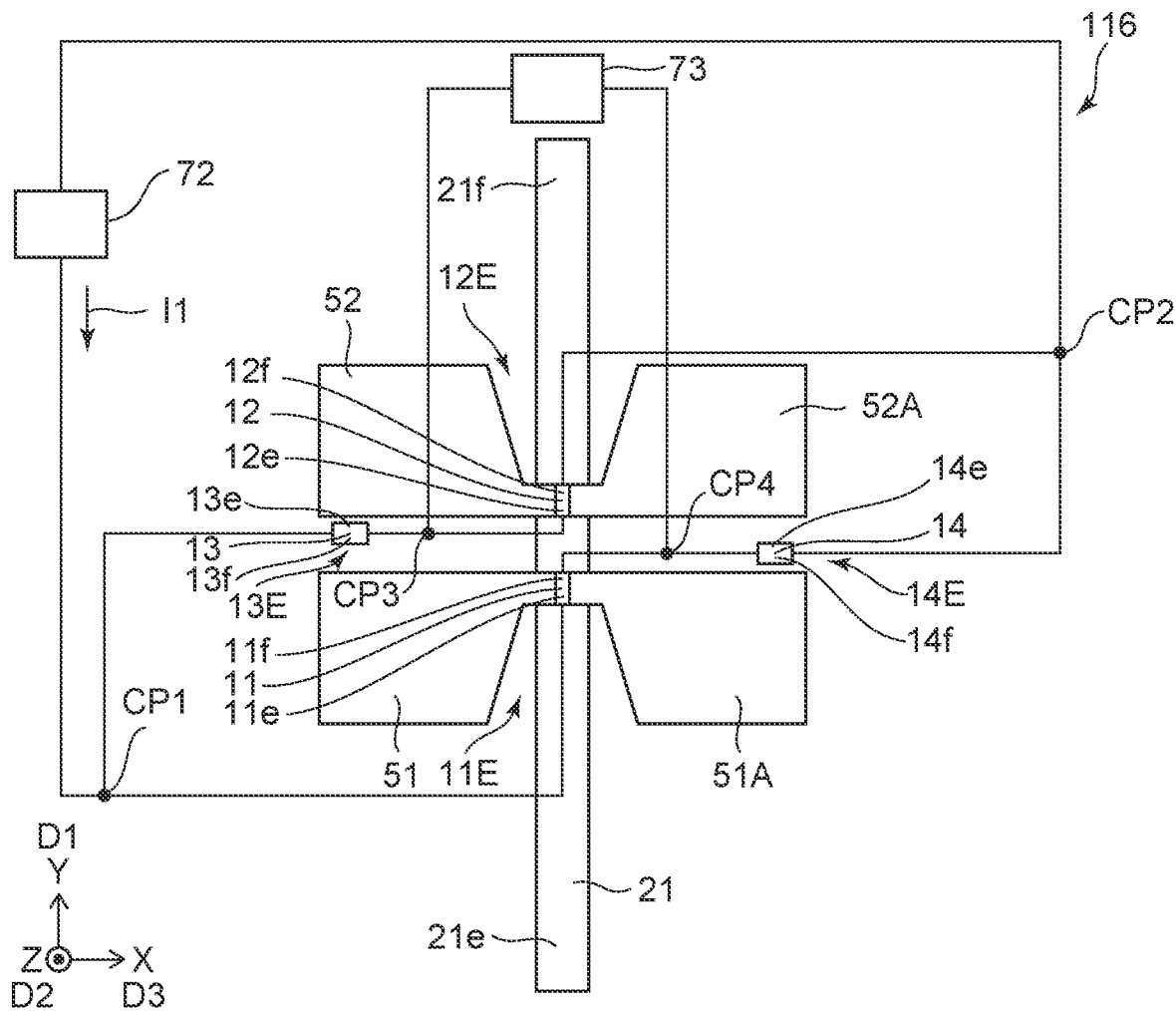
FIG. 16 is a schematic plan view illustrating the magnetic sensor according to the first embodiment.

FIGS. 15 and 16 are schematic plan views illustrating the magnetic sensor according to the first embodiment.

As shown in FIG. 15, a magnetic sensor 116 according to the embodiment includes the first element portion 11E, the second element portion 12E, the third element portion 13E and the fourth element portion 14E. The first element portion 11E in the magnetic sensor 116 may be the same as the first element portion 11E in the magnetic sensor 110 or the magnetic sensor In the magnetic sensor 116, the second element portion 12E includes the second magnetic element 12, the second magnetic member 52 and the second opposing magnetic member 52A. The second magnetic element 12 includes the second end portion 12e and the second other end portion 12f. The direction from the second end portion 12e to the second other end portion 12f is along the first direction D1.

The direction from a part of the first conductive member 21 to the second magnetic element 12 is along the second direction D2. The part of the first conductive member 21 overlaps the second magnetic element 12 in the second direction D2.

The position of at least part of the second magnetic element 12 in the third direction D3 is between the position of the second magnetic member 52 in the third direction D3 and the position of the second opposing magnetic member 52A in the third direction D3.

The third element portion 13E includes the third magnetic element 13. The third magnetic element 13 includes the third end portion 13e and the third other end portion 13f. The fourth element portion 14E includes the fourth magnetic element 14. The fourth magnetic element 14 includes the fourth end portion 14e and the fourth other end portion 14f.

As shown in FIG. 16, in the magnetic sensor 116, the first end portion 11e is electrically connected to the third end portion 13e. The first other end portion 11f is electrically connected to the fourth end portion 14e. The third other end portion 13f is electrically connected to the second end portion 12e. The second other end portion 12f is electrically connected to the fourth other end portion 14f.

The third magnetic element 13 and the fourth magnetic element 14 do not overlap the first magnetic member 51, the first opposing magnetic member 51A, the second magnetic member 52 and the second opposing magnetic member 52A in the second direction D2.

In this example, the position of the third magnetic element 13 in the first direction D1 is between the position of the first magnetic member 51 in the first direction D1 and the position of the second magnetic member 52 in the first direction D1. The position of the fourth magnetic element 14 in the first direction D1 is between the position of the first opposing magnetic member 51A in the first direction D1 and the position of the second opposing magnetic member 52A in the first direction D1.

As shown in FIG. 15, the first circuit 71 can supply the first current I1 including an AC component between the first conductive portion 21e and the first other conductive portion 21f.

As shown in FIG. 16, the second circuit 72 can supply the element current Id or the element voltage between the first connection point CP1 of the first end portion 11e and the third end portion 13e and the second connection point of the second other end portion 12f and the fourth other end portion 14f.

The third circuit 73 can output signal Sg1 corresponding to the electrical signal generated between the third connection point CP3 of the third other end portion 13f and the second end portion 12e and the fourth connection point CP4 of the first other end portion 11f and the fourth end portion 14e.

Second Embodiment

The second embodiment relates to an inspection device. As will be described later, the inspection device may include a diagnostic device.

Figure 17:
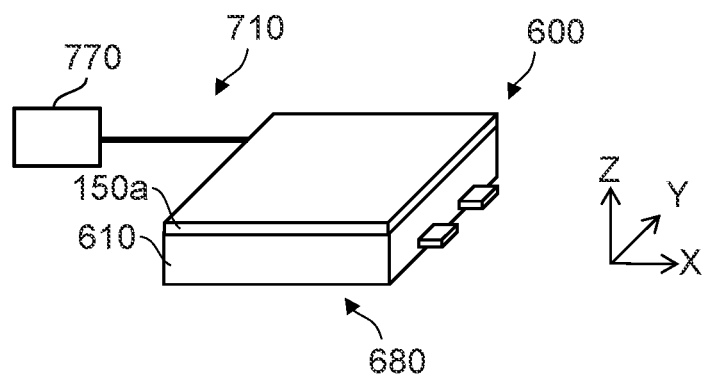
FIG. 17 is a schematic perspective view illustrating an inspection device according to a second embodiment.

FIG. 17 is a schematic perspective view illustrating an inspection device according to a second embodiment.

As shown in FIG. 17, an inspection device 710 according to the embodiment includes a sensor 150a (magnetic sensor) and a processor 770. The sensor 150a may be the sensor according to the first embodiment and a modification thereof. The processor 770 processes an output signal obtained from the sensor 150a. The processor 770 may compare the signal obtained from the sensor 150a with the reference value. The processor 770 can output the inspection result based on the processing result.

For example, the inspection device 710 inspects an inspection object 680. The inspection object 680 is, for example, an electronic device (including a semiconductor circuit or the like). The inspection object 680 may be, for example, a battery 610 or the like.

For example, the sensor 150a according to the embodiment may be used together with the battery 610. For example, a battery system 600 includes the battery 610 and the sensor 150a. The sensor 150a can detect the magnetic field generated by the current flowing through the battery 610.

Figure 18:
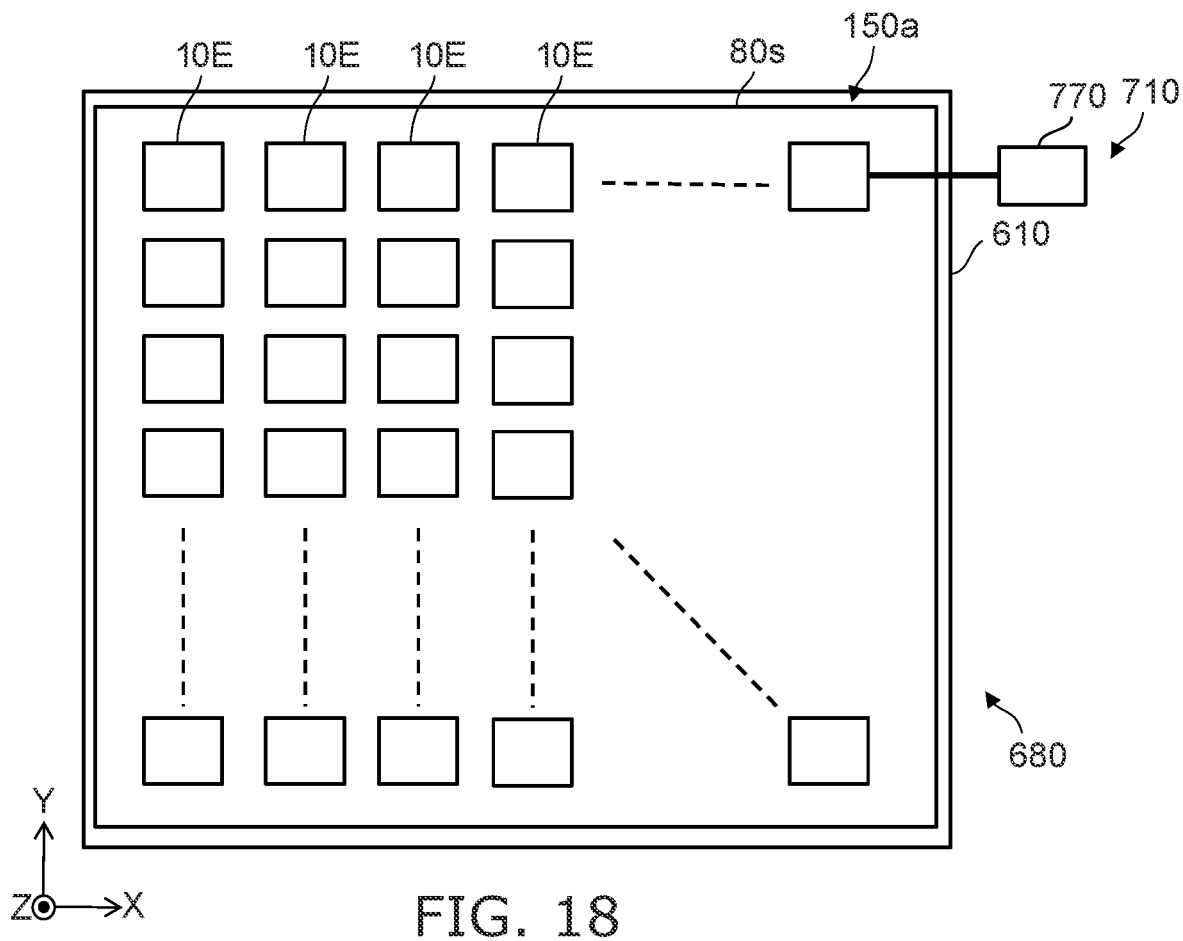
FIG. 18 is a schematic plan view illustrating the inspection device according to the second embodiment.

FIG. 18 is a schematic plan view illustrating the inspection device according to the second embodiment.

As shown in FIG. 18, the sensor 150a includes, for example, multiple sensors according to the embodiment. In this example, the sensor 150a includes multiple sensors (the element portion 10U such as the sensor 110, etc.). The multiple sensors are arranged along, for example, two directions (for example, the X-axis direction and the Y-axis direction). The multiple magnetic sensors 110 are provided, for example, on a substrate.

The sensor 150a can detect the magnetic field generated by the current flowing through the inspection object 680 (for example, the battery 610 may be used). For example, when the battery 610 approaches an abnormal state, an abnormal current may start to flow through the battery 610. By detecting the abnormal current with the sensor 150a, it is possible to know the change in the state of the battery 610. For example, in a state where the sensor 150a is placed close to the battery 610, the entire battery 610 can be inspected in a short time by moving the sensor array in two directions. The sensor 150a may be used for inspection of the battery 610 in manufacturing process of the battery 610.

The sensor according to the embodiment can be applied to, for example, the inspection device 710 such as a diagnostic device.

Figure 19:
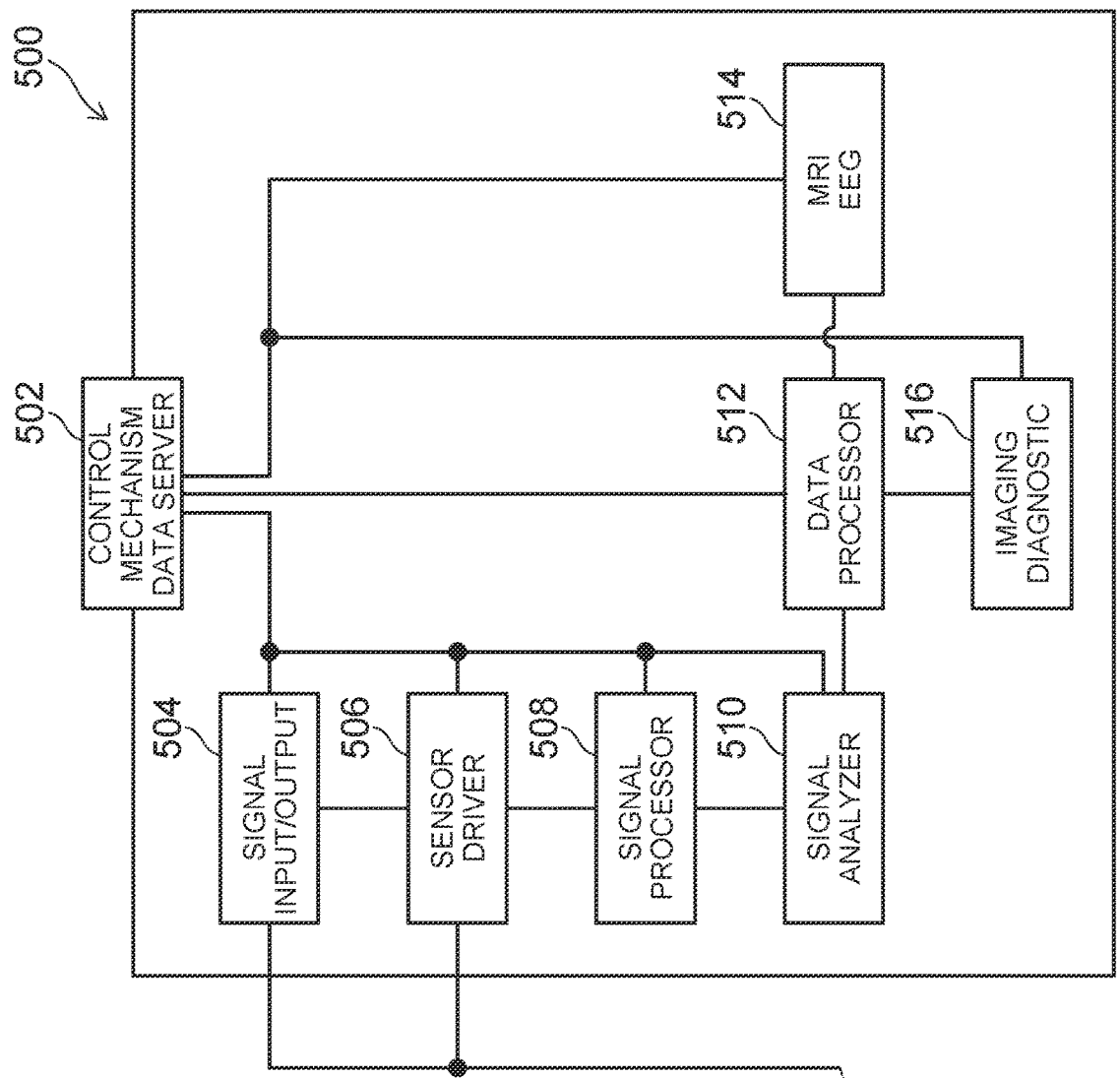
FIG. 19 is a schematic diagram illustrating the sensor and the inspection device according to the embodiment.
Figure 19:
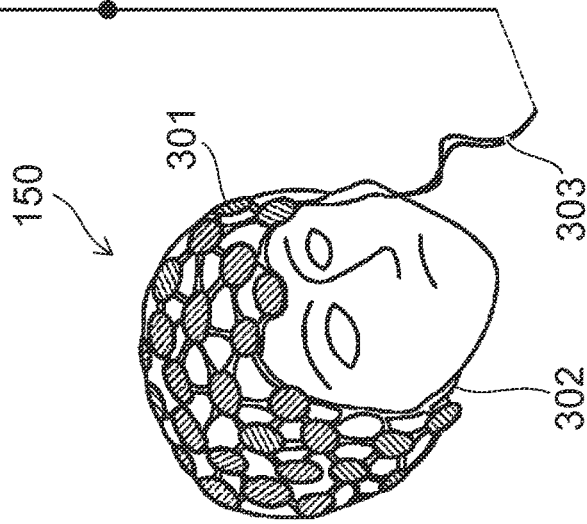

FIG. 19 is a schematic diagram illustrating the sensor and the inspection device according to the embodiment.

As shown in FIG. 19, a diagnostic apparatus 500, which is an example of the inspection device 710, includes a sensor 150. The sensor 150 includes the sensors described with respect to the first embodiment and modifications thereof.

In the diagnostic apparatus 500, the sensor 150 is, for example, a magnetoencephalograph. The magnetoencephalograph detects the magnetic field generated by the cranial nerves. When the sensor 150 is used in a magnetoencephalograph, the size of the magnetic element included in the sensor 150 is, for example, not less than 1 mm and less than 10 mm. This size is, for example, the length including an MFC.

As shown in FIG. 19, the sensor 150 (magnetoencephalogram) is attached to, for example, the head of a human body. The sensor 150 (magnetoencephalogram) includes a sensor part 301. The sensor 150 (magnetoencephalogram) may include multiple sensor parts 301. The number of the multiple sensor parts 301 is, for example, about 100 (for example, not less than 50 and not more than 150). The multiple sensor parts 301 are provided on a flexible base body 302.

The sensor 150 may include, for example, a circuit such as differential detection. The sensor 150 may include a sensor other than the sensor (for example, a potential terminal or an acceleration sensor).

A size of the sensor 150 is smaller than a size of a conventional SQUID sensor. Therefore, it is easy to install the multiple sensor parts 301. Installation of the multiple sensor parts 301 and other circuits is easy. The coexistence of the multiple sensor parts 301 and other sensors is easy.

The base body 302 may include an elastic body such as a silicone resin. For example, the multiple sensor parts 301 are provided to be connected to the base body 302. The base body 302 can be in close contact with the head, for example.

The input/output code 303 of the sensor part 301 is connected to a sensor driver 506 and a signal input/output 504 of the diagnostic apparatus 500. The magnetic field measurement is performed in the sensor part 301 based on the electric power from the sensor driver 506 and the control signal from the signal input/output 504. The result is input to the signal input/output 504. The signal obtained by the signal input/output 504 is supplied to a signal processor 508. The signal processor 508 performs processing such as noise removal, filtering, amplification, and signal calculation. The signal processed by the signal processor 508 is supplied to a signal analyzer 510. The signal analyzer 510 extracts, for example, a specific signal for magnetoencephalography measurement. In the signal analyzer 510, for example, signal analysis for matching signal phases is performed.

The output of the signal analyzer 510 (data for which signal analysis has been completed) is supplied to a data processor 512. The data processor 512 performs data analysis. In this data analysis, for example, image data such as MRI (Magnetic Resonance Imaging) can be incorporated. In this data analysis, for example, scalp potential information such as EEG (Electroencephalogram) can be incorporated. For example, a data part 514 such as MRI or EEG is connected to the data processor 512. By the data analysis, for example, nerve ignition point analysis, inverse problem analysis, and the like are performed.

The result of the data analysis is supplied to, for example, an imaging diagnostic 516. Imaging is performed in the imaging diagnostic 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnostic apparatus 500 according to the embodiment includes the sensor 150 and the processor that processes an output signal obtained from the sensor 150. This processor includes, for example, at least one of a signal processor 508 or a data processor 512. The processor includes, for example, a computer.

In the sensor 150 shown in FIG. 19, the sensor part 301 is installed on the head of the human body. The sensor part 301 may be installed on the chest of the human body. This enables magnetocardiography measurement. For example, the sensor part 301 may be installed on the abdomen of a pregnant woman.

This makes it possible to perform a fetal heartbeat test.

The sensor device including the subject is preferably installed in a shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with a shield mechanism. For example, effective shielding may be performed in the signal analysis or the data processing.

In embodiments, the base body 302 may be flexible and may be substantially non-flexible. In the example shown in FIG. 19, the base body 302 is a continuous film processed into a hat shape. The base body 302 may be in a net shape. Thereby, for example, good wearability can be obtained. For example, the adhesion of the base body 302 to the human body is improved. The base body 302 may be helmet-shaped and may be rigid.

Figure 20:
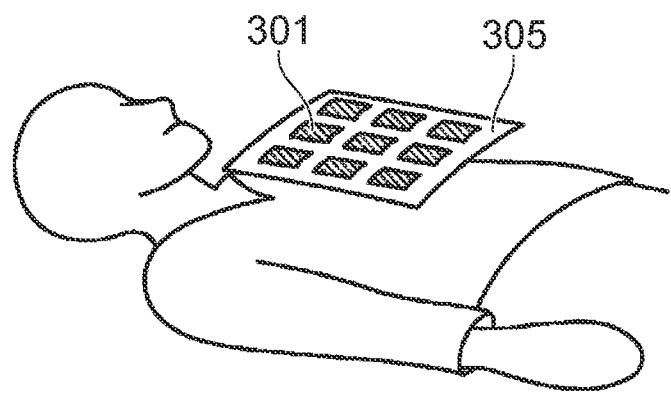
FIG. 20 is a schematic view illustrating the inspection device according to the embodiment.

FIG. 20 is a schematic view illustrating the inspection device according to the embodiment.

In the example shown in FIG. 20, the sensor part 301 is provided on a flat plate-shaped hard base body 305.

In the example shown in FIG. 20, the input/output of the signal obtained from the sensor part 301 is the same as the input/output described with respect to FIG. 19. In the example shown in FIG. 20, the processing of the signal obtained from the sensor part 301 is the same as the processing described with respect to FIG. 19.

There is a reference example of using a SQUID (Superconducting Quantum Interference Device) sensor as a device for measuring a weak magnetic field such as a magnetic field generated from a living body. In this reference example, since superconductivity is used, the device is large and the power consumption is also large. The burden on the measurement target (patient) is heavy.

According to the embodiment, the device can be downsized. Power consumption can be suppressed. The burden on the measurement object (patient) can be reduced. According to the embodiment, the SN ratio of magnetic field detection can be improved. Sensitivity can be improved.

The embodiments may include the following configurations (for example, technical proposals).

(Configuration 1)

A magnetic sensor, comprising:
a first element portion including a first magnetic element, a first conductive member, a first magnetic member and a first opposing magnetic member,
the first magnetic element including a first end portion and a first other end portion, a direction from the first end portion to the first other end portion being along a first direction,
a second direction from the first conductive member to the first magnetic element crossing the first direction,
a third direction from the first magnetic member to the first opposing magnetic member crossing a plane including the first direction and the second direction,
a position of at least a part of the first magnetic element in the third direction being between a position of the first magnetic member in the third direction and a position of the first opposing magnetic member in the third direction,
the first magnetic member including a first other magnetic portion and a first magnetic portion, a direction from the first other magnetic portion to the first magnetic portion being along the third direction, a first other magnetic portion length along the first direction of the first other magnetic portion being longer than a first magnetic portion length along the first direction of the first magnetic portion, and
the first conductive member overlapping the first magnetic portion in the second direction, and the first conductive member not overlapping the first other magnetic portion in the second direction.

(Configuration 2)

The sensor according to Configuration 1, wherein
the first magnetic member further includes a first intermediate magnetic portion,
the first intermediate magnetic portion is between the first other magnetic portion and the first magnetic portion in the third direction,
a first intermediate magnetic portion length along the first direction of the first intermediate magnetic portion is between the first other magnetic portion length and the first magnetic portion length, the first intermediate magnetic portion length varies in the third direction, a rate of change in the third direction of the first magnetic portion length is lower than a rate of change in the third direction of the first intermediate magnetic portion length in the third direction, and the first conductive member does not overlap the first intermediate magnetic portion in the second direction.

(Configuration 3)

The sensor according to Configuration 2, wherein the first magnetic portion length is substantially constant.

(Configuration 4)

The sensor according to Configuration 2 or 3, wherein a first ratio is less than 1, the first ratio being a ratio of a sum of a length of the first magnetic portion along the third direction and a length of the first intermediate magnetic portion along the third direction to a length of the first other magnetic portion along the third direction.

(Configuration 5)

The sensor according to Configuration 4, wherein the first ratio is 0.5 or less.

(Configuration 6)

The sensor according to any one of Configurations 1 to 5, wherein the first conductive member includes a first conductive portion and a first other conductive portion, a direction from the first conductive portion to the first other conductive portion is along the first direction, a distance between the first conductive portion and the first end portion is shorter than a distance between the first conductive portion and the first other end portion, and a distance between the first other conductive portion and the first other end portion is shorter than the distance between the first other conductive portion and the first end portion.

(Configuration 7)

The sensor according to Configuration 6, further comprising a circuit portion including a first circuit, the first circuit being configured to supply a first current including an AC component to the first conductive member.

(Configuration 8)

The sensor according to Configuration 7, wherein the circuit portion further includes a second circuit and a third circuit, the second circuit is configured to supply an element current or an element voltage to the first magnetic element, and the third circuit is configured to output a signal corresponding to a first electrical resistance of the first magnetic element.

(Configuration 9)

The sensor according to Configuration 6, further comprising a second element unit, the second element portion including a second magnetic element, a second conductive member, a second magnetic member and a second opposing magnetic member, the second magnetic element including a second end portion and a second other end portion, a direction from the second end portion to the second other end portion being along the first direction, a direction from the second conductive member to the second magnetic element being along the second direction, the second conductive member including a second conductive portion and a second other conductive portion, a direction from the second conductive portion to the second other conductive portion being along the first direction, a distance between the second conductive portion and the second end portion being shorter than a distance between the second conductive portion and the second other end portion, a distance between the second other conductive portion and the second other end portion being shorter than a distance between the second other conductive portion and the second end portion, a position of at least a part of the second magnetic element in the third direction being between a position of the second magnetic member in the third direction and a position of the second opposing magnetic member in the third direction, the first other end portion being electrically connected to the second end portion, and the first other conductive portion being electrically connected to the second conductive portion.

(Configuration 10)

The sensor according to Configuration 9, wherein the second magnetic member includes a second other magnetic portion and a second magnetic portion, a direction from the second other magnetic portion to the second magnetic portion is along the third direction, a second other magnetic portion length along the first direction of the second other magnetic portion is longer than a second magnetic portion length along the first direction of the second magnetic portion, the second conductive member overlaps the second magnetic portion in the second direction, and the second conductive member does not overlap the second other magnetic portion in the second direction.

(Configuration 11)

The sensor according to Configuration 9 or 10, wherein the second magnetic member is continuous with the first magnetic member, and the second opposing magnetic member is continuous with the first opposing magnetic member.

(Configuration 12)

The sensor according to Configuration 9, further comprising a third element portion and a fourth element portion, the third element portion including a third magnetic element, a third conductive member, a third magnetic member and a third opposing magnetic member, the third magnetic element including a third end portion and a third other end portion, a direction from the third end portion to the third other end portion being along the first direction, a direction from the third conductive member to the third magnetic element being along the second direction, the third conductive member including a third conductive portion and a third other conductive portion, a direction from the third conductive portion to the third other conductive portion being along the first direction, a distance between the third conductive portion and the third end portion being shorter than a distance between the third conductive portion and the third other end portion, a distance between the third other conductive portion and the third other end portion being shorter than a distance between the third other conductive portion and the third end portion, a position of at least a part of the third magnetic element in the third direction being between a position of the third magnetic member in the third direction and a position of the third opposing magnetic member in the third direction, the fourth element portion including a fourth magnetic element, a fourth conductive member, a fourth magnetic member and a fourth opposing magnetic member, the fourth magnetic element including a fourth end portion and a fourth other end portion, a direction from the fourth end portion to the fourth other end portion being along the first direction, a direction from the fourth conductive member to the fourth magnetic element being along the second direction, the fourth conductive member including a fourth conductive portion and a fourth other conductive portion, a direction from the fourth conductive portion to the fourth other conductive portion being along the first direction, a distance between the fourth conductive portion and the fourth end portion being shorter than a distance between the fourth conductive portion and the fourth other end portion, a distance between the fourth other conductive portion and the fourth other end portion being shorter than the distance between the fourth other conductive portion and the fourth end portion, a position of at least a part of the fourth magnetic element in the third direction being between the position of the fourth magnetic member in the third direction and a position of the fourth opposing magnetic member in the third direction, the second other end portion being electrically connected to the fourth other end portion, the third end portion being electrically connected to the first end portion, the third other end portion being electrically connected to the fourth end portion, the second other conductive portion being electrically connected to the fourth other conductive portion, the third conductive portion being electrically connected to the first conductive portion, and the third conductive portion being electrically connected to the fourth conductive portion.

(Configuration 13)

The sensor according to Configuration 12, further comprising a circuit portion, the circuit portion including a first circuit, a second circuit and a third circuit, the first circuit being configured to supply a first current including an AC component between the first other conductive portion and the third other conductive portion, the second circuit being configured to supply an element current or an element voltage between a first connection point of the first end portion and the third end portion and a second connection point between the second other end portion and the fourth other end portion, and the third circuit being configured to output a signal corresponding to an electrical signal generated between a third connection point of the first other end portion and the second end portion and a fourth connection point of the third other end portion and the fourth end portion.

(Configuration 14)

The sensor according to Configuration 13, wherein the third magnetic member includes a third other magnetic portion and a third magnetic portion, a direction from the third other magnetic portion to the third magnetic portion is along the third direction, a third magnetic portion length of the third magnetic portion along the first direction is longer than a third magnetic portion length of the third magnetic portion along the first direction, the third conductive member overlaps the third magnetic portion in the second direction, the third conductive member does not overlap the third other magnetic portion in the second direction, the fourth magnetic member includes a fourth other magnetic portion and a fourth magnetic portion, a direction from the fourth other magnetic portion to the fourth magnetic portion is along the third direction, a fourth other magnetic portion length along the first direction of the fourth other magnetic portion is longer than a fourth magnetic portion length along the first direction of the fourth magnetic portion, the fourth conductive member overlaps the fourth magnetic portion in the second direction, and the fourth conductive member does not overlap the fourth other magnetic portion in the second direction.

(Configuration 15)

The sensor according to any one of Configurations 12 to 14, wherein the third magnetic member is continuous with the first opposing magnetic member, and the fourth magnetic member is continuous with the second opposing magnetic member.

(Configuration 16)

The sensor according to Configuration 6, further comprising a second element portion, a third element portion, and a fourth element portion, the second element portion including a second magnetic element and a second conductive member, the second magnetic element including a second end portion and a second other end portion, a direction from the second end portion to the second other end portion being along the first direction, a direction from the second conductive member to the second magnetic element being along the second direction, the second conductive member including a second conductive portion and a second other conductive portion, a direction from the second conductive portion to the second other conductive portion being along the first direction, a distance between the second conductive portion and the second end portion being shorter than a distance between the second conductive portion and the second other end portion, a distance between the second other conductive portion and the second other end portion being shorter than the distance between the second other conductive portion and the second end portion, the third element portion including a third magnetic element and a third conductive member, the third magnetic element including a third end portion and a third other end portion, ae direction from the third end portion to the third other end portion being along the first direction, a direction from the third conductive member to the third magnetic element being along the second direction, the third conductive member including a third conductive portion and a third other conductive portion, a direction from the third conductive portion to the third other conductive portion being along the first direction, a distance between the third conductive portion and the third end portion being shorter than a distance between the third conductive portion and the third other end portion, a distance between the third other conductive portion and the third other end portion being shorter than a distance between the third other conductive portion and the third end portion, the fourth element portion including a fourth magnetic element, a fourth conductive member, a fourth magnetic member and a fourth opposing magnetic member, the fourth magnetic element including a fourth end portion and a fourth other end portion, a direction from the fourth end portion to the fourth other end portion being along the first direction, a direction from the fourth conductive member to the fourth magnetic element being along the second direction, the fourth conductive member including a fourth conductive portion and a fourth other conductive portion, a direction from the fourth conductive portion to the fourth other conductive portion being along the first direction, a distance between the fourth conductive portion and the fourth end portion being shorter than the distance between the fourth conductive portion and the fourth other end portion, a distance between the fourth other conductive portion and the fourth other end portion being shorter than the distance between the fourth other conductive portion and the fourth end portion, a position of at least a part of the fourth magnetic element in the third direction being between a position of the fourth magnetic member in the third direction and a position of the fourth opposing magnetic member in the third direction, the first other end portion being electrically connected to the second end portion, the first other conductive portion being electrically connected to the second conductive portion, the second other end portion being electrically connected to the fourth other end portion, the third end portion being electrically connected to the first end portion, the third other end portion being electrically connected to the fourth end portion, the second other conductive portion being electrically connected to the fourth other conductive portion, the third conductive portion being electrically connected to the first conductive portion, and the third conductive portion being electrically connected to the fourth conductive portion.

(Configuration 17)

The sensor according to Configuration 16, further comprising a circuit portion, the circuit portion including a first circuit, a second circuit and a third circuit, the first circuit being configured to supply a first current including an AC component between the first other conductive portion and the third other conductive portion, the second circuit being configured to supply an element current or an element voltage between a first connection point of the first end portion and the third end portion and a second connection point of the second other end portion and the fourth other end portion, and the third circuit being configured to output a signal corresponding to an electrical signal generated between a third connection point of the first other end portion and the second end portion and a fourth connection point of the third other end portion and the fourth end portion.

(Configuration 18)

The sensor according to Configuration 6, further comprising a second element portion, a third element portion, and a fourth element portion, the second element portion including a second magnetic element, a second magnetic member and a second opposing magnetic member, the second magnetic element including a second end portion and a second other end portion, a direction from the second end portion to the second other end portion being along the first direction, a direction from the portion of the first conductive member to the second magnetic element being along the second direction, a position of at least a part of the second magnetic element in the third direction being between a position of the second magnetic member in the third direction and a position of the second opposing magnetic member in the third direction, the third element unit including a third magnetic element, the third magnetic element including a third end portion and a third other end portion, the fourth element portion including a fourth magnetic element, the fourth magnetic element including a fourth end portion and a fourth other end portion, the first end portion being electrically connected to the third end portion, the first other end portion being electrically connected to the fourth end portion, the third other end portion being electrically connected to the second end portion, the second other end portion being electrically connected to the fourth other end portion, and the third magnetic element and the fourth magnetic element not overlapping the first magnetic member, the first opposing magnetic member, the second magnetic member, and the second opposing magnetic member in the second direction.

(Configuration 19)

The sensor according to Configuration 18, further comprising a circuit portion, the circuit portion including a first circuit, a second circuit and a third circuit, the first circuit being configured to supply a first current including an AC component between the first conductive portion and the first other conductive portion, the second circuit being configured to supply an element current or an element voltage between a first connection point of the first end portion and the third end portion and a second connection point of the second other end portion and the fourth other end portion, and the third circuit being configured to output a signal corresponding to an electrical signal generated between a third connection point of the third other end portion and the second end portion and a fourth connection point of the first other end portion and the fourth end portion.

(Configuration 20)

An inspection device, comprising:
the magnetic sensor according to any one of Configurations 1 to 19; and
a processor configured to process an output signal obtained from the magnetic sensor.

According to the embodiment, it is possible to provide a magnetic sensor and an inspection device capable of improving the characteristics.

In the present specification, "perpendicular" and "parallel" include not only strict perpendicularity and strict parallelism, but also variations in the manufacturing process, for example, and may be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in the magnetic sensors such as element portions, magnetic elements, magnetic layers, non-magnetic layers, conductive members, conductive layers circuit, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors and all inspection devices practicable by an appropriate design modification by one skilled in the art based on the magnetic sensors and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
a first element portion including a first magnetic element, a first conductive member, a first magnetic member and a first opposing magnetic member,
the first magnetic element extending along a first direction, a length of the first magnetic element along the first direction being longer than a length of the first magnetic element along a third direction crossing the first direction,
the first magnetic element including a first end portion and a first other end portion, a direction from the first end portion to the first other end portion being along the first direction,
a second direction from the first conductive member to the first magnetic element crossing a plane including the first direction and the third direction,
a direction from the first magnetic member to the first opposing magnetic member being along the third direction,
a position of at least a part of the first magnetic element in the third direction being between a position of the first magnetic member in the third direction and a position of the first opposing magnetic member in the third direction,
the first magnetic member including a first other magnetic portion and a first magnetic portion, a direction from the first other magnetic portion to the first magnetic portion being along the third direction, a first other magnetic portion length along the first direction of the first other magnetic portion being longer than a first magnetic portion length along the first direction of the first magnetic portion, and
the first conductive member overlapping the first magnetic portion in the second direction, and the first conductive member not overlapping the first other magnetic portion in the second direction.

2. The sensor according to claim 1, wherein
the first magnetic member further includes a first intermediate magnetic portion,
the first intermediate magnetic portion is between the first other magnetic portion and the first magnetic portion in the third direction,
a first intermediate magnetic portion length along the first direction of the first intermediate magnetic portion is between the first other magnetic portion length and the first magnetic portion length,
the first intermediate magnetic portion length varies in the third direction,
a rate of change in the third direction of the first magnetic portion length is lower than a rate of change in the third direction of the first intermediate magnetic portion length in the third direction, and
the first conductive member does not overlap the first intermediate magnetic portion in the second direction.

3. The sensor according to claim 2, wherein the first magnetic portion length is substantially constant.

4. The sensor according to claim 2, wherein
a first ratio is less than 1,
the first ratio being a ratio of a sum of a length of the first magnetic portion along the third direction and a length of the first intermediate magnetic portion along the third direction to a length of the first other magnetic portion along the third direction.

5. The sensor according to claim 4, wherein the first ratio is 0.5 or less.

6. The sensor according to claim 1, wherein
the first conductive member includes a first conductive portion and a first other conductive portion,
a direction from the first conductive portion to the first other conductive portion is along the first direction,
a distance between the first conductive portion and the first end portion is shorter than a distance between the first conductive portion and the first other end portion, and a distance between the first other conductive portion and the first other end portion is shorter than the distance between the first other conductive portion and the first end portion.

7. The sensor according to claim 6, further comprising a circuit portion including a first circuit,
the first circuit being configured to supply a first current including an AC component to the first conductive member.

8. The sensor according to claim 7, wherein
the circuit portion further includes a second circuit and a third circuit,
the second circuit is configured to supply an element current or an element voltage to the first magnetic element, and
the third circuit is configured to output a signal corresponding to a first electrical resistance of the first magnetic element.

9. The sensor according to claim 6, further comprising a second element portion,
the second element portion including a second magnetic element, a second conductive member, a second magnetic member and a second opposing magnetic member,
the second magnetic element including a second end portion and a second other end portion, a direction from the second end portion to the second other end portion being along the first direction,
a direction from the second conductive member to the second magnetic element being along the second direction,
the second conductive member including a second conductive portion and a second other conductive portion,
a direction from the second conductive portion to the second other conductive portion being along the first direction,
a distance between the second conductive portion and the second end portion being shorter than a distance between the second conductive portion and the second other end portion,
a distance between the second other conductive portion and the second other end portion being shorter than a distance between the second other conductive portion and the second end portion,
a position of at least a part of the second magnetic element in the third direction being between a position of the second magnetic member in the third direction and a position of the second opposing magnetic member in the third direction,
the first other end portion being electrically connected to the second end portion, and
the first other conductive portion being electrically connected to the second conductive portion.

10. The sensor according to claim 9, wherein
the second magnetic member includes a second other magnetic portion and a second magnetic portion,
a direction from the second other magnetic portion to the second magnetic portion is along the third direction,
a second other magnetic portion length along the first direction of the second other magnetic portion is longer than a second magnetic portion length along the first direction of the second magnetic portion,
the second conductive member overlaps the second magnetic portion in the second direction, and
the second conductive member does not overlap the second other magnetic portion in the second direction.

11. The sensor according to claim 9, wherein
the second magnetic member is continuous with the first magnetic member, and
the second opposing magnetic member is continuous with the first opposing magnetic member.

12. The sensor according to claim 9, further comprising a third element portion and a fourth element portion,
the third element portion including a third magnetic element, a third conductive member, a third magnetic member and a third opposing magnetic member,
the third magnetic element including a third end portion and a third other end portion, a direction from the third end portion to the third other end portion being along the first direction,
a direction from the third conductive member to the third magnetic element being along the second direction,
the third conductive member including a third conductive portion and a third other conductive portion,
a direction from the third conductive portion to the third other conductive portion being along the first direction,
a distance between the third conductive portion and the third end portion being shorter than a distance between the third conductive portion and the third other end portion,
a distance between the third other conductive portion and the third other end portion being shorter than a distance between the third other conductive portion and the third end portion,
a position of at least a part of the third magnetic element in the third direction being between a position of the third magnetic member in the third direction and a position of the third opposing magnetic member in the third direction,
the fourth element portion including a fourth magnetic element, a fourth conductive member, a fourth magnetic member and a fourth opposing magnetic member,
the fourth magnetic element including a fourth end portion and a fourth other end portion, a direction from the fourth end portion to the fourth other end portion being along the first direction,
a direction from the fourth conductive member to the fourth magnetic element being along the second direction,
the fourth conductive member including a fourth conductive portion and a fourth other conductive portion,
a direction from the fourth conductive portion to the fourth other conductive portion being along the first direction,
a distance between the fourth conductive portion and the fourth end portion being shorter than a distance between the fourth conductive portion and the fourth other end portion,
a distance between the fourth other conductive portion and the fourth other end portion being shorter than the distance between the fourth other conductive portion and the fourth end portion,
a position of at least a part of the fourth magnetic element in the third direction being between the position of the fourth magnetic member in the third direction and a position of the fourth opposing magnetic member in the third direction,
the second other end portion being electrically connected to the fourth other end portion,
the third end portion being electrically connected to the first end portion,
the third other end portion being electrically connected to the fourth end portion, the second other conductive portion being electrically connected to the fourth other conductive portion, the third conductive portion being electrically connected to the first conductive portion, and the third conductive portion being electrically connected to the fourth conductive portion.

13. The sensor according to claim 12, further comprising a circuit portion, the circuit portion including a first circuit, a second circuit and a third circuit, the first circuit being configured to supply a first current including an AC component between the first other conductive portion and the third other conductive portion, the second circuit being configured to supply an element current or an element voltage between a first connection point of the first end portion and the third end portion and a second connection point between the second other end portion and the fourth other end portion, and the third circuit being configured to output a signal corresponding to an electrical signal generated between a third connection point of the first other end portion and the second end portion and a fourth connection point of the third other end portion and the fourth end portion.

14. The sensor according to claim 13, wherein the third magnetic member includes a third other magnetic portion and a third magnetic portion, a direction from the third other magnetic portion to the third magnetic portion is along the third direction, a third magnetic portion length of the third magnetic portion along the first direction is longer than a third magnetic portion length of the third magnetic portion along the first direction, the third conductive member overlaps the third magnetic portion in the second direction, the third conductive member does not overlap the third other magnetic portion in the second direction, the fourth magnetic member includes a fourth other magnetic portion and a fourth magnetic portion, a direction from the fourth other magnetic portion to the fourth magnetic portion is along the third direction, a fourth other magnetic portion length along the first direction of the fourth other magnetic portion is longer than a fourth magnetic portion length along the first direction of the fourth magnetic portion, the fourth conductive member overlaps the fourth magnetic portion in the second direction, and the fourth conductive member does not overlap the fourth other magnetic portion in the second direction.

15. The sensor according to claim 12, wherein the third magnetic member is continuous with the first opposing magnetic member, and the fourth magnetic member is continuous with the second opposing magnetic member.

16. The sensor according to claim 6, further comprising a second element portion, a third element portion, and a fourth element portion, the second element portion including a second magnetic element and a second conductive member, the second magnetic element including a second end portion and a second other end portion, a direction from the second end portion to the second other end portion being along the first direction, a direction from the second conductive member to the second magnetic element being along the second direction, the second conductive member including a second conductive portion and a second other conductive portion, a direction from the second conductive portion to the second other conductive portion being along the first direction, a distance between the second conductive portion and the second end portion being shorter than a distance between the second conductive portion and the second other end portion, a distance between the second other conductive portion and the second other end portion being shorter than the distance between the second other conductive portion and the second end portion, the third element portion including a third magnetic element and a third conductive member, the third magnetic element including a third end portion and a third other end portion, ae direction from the third end portion to the third other end portion being along the first direction, a direction from the third conductive member to the third magnetic element being along the second direction, the third conductive member including a third conductive portion and a third other conductive portion, a direction from the third conductive portion to the third other conductive portion being along the first direction, a distance between the third conductive portion and the third end portion being shorter than a distance between the third conductive portion and the third other end portion, a distance between the third other conductive portion and the third other end portion being shorter than a distance between the third other conductive portion and the third end portion, the fourth element portion including a fourth magnetic element, a fourth conductive member, a fourth magnetic member and a fourth opposing magnetic member, the fourth magnetic element including a fourth end portion and a fourth other end portion, a direction from the fourth end portion to the fourth other end portion being along the first direction, a direction from the fourth conductive member to the fourth magnetic element being along the second direction, the fourth conductive member including a fourth conductive portion and a fourth other conductive portion, a direction from the fourth conductive portion to the fourth other conductive portion being along the first direction, a distance between the fourth conductive portion and the fourth end portion being shorter than the distance between the fourth conductive portion and the fourth other end portion, a distance between the fourth other conductive portion and the fourth other end portion being shorter than the distance between the fourth other conductive portion and the fourth end portion, a position of at least a part of the fourth magnetic element in the third direction being between a position of the fourth magnetic member in the third direction and a position of the fourth opposing magnetic member in the third direction, the first other end portion being electrically connected to the second end portion, the first other conductive portion being electrically connected to the second conductive portion, the second other end portion being electrically connected to the fourth other end portion, the third end portion being electrically connected to the first end portion, the third other end portion being electrically connected to the fourth end portion, the second other conductive portion being electrically connected to the fourth other conductive portion, the third conductive portion being electrically connected to the first conductive portion, and the third conductive portion being electrically connected to the fourth conductive portion.

17. The sensor according to claim 16, further comprising a circuit portion, the circuit portion including a first circuit, a second circuit and a third circuit, the first circuit being configured to supply a first current including an AC component between the first other conductive portion and the third other conductive portion, the second circuit being configured to supply an element current or an element voltage between a first connection point of the first end portion and the third end portion and a second connection point of the second other end portion and the fourth other end portion, and the third circuit being configured to output a signal corresponding to an electrical signal generated between a third connection point of the first other end portion and the second end portion and a fourth connection point of the third other end portion and the fourth end portion.

18. The sensor according to claim 6, further comprising a second element portion, a third element portion, and a fourth element portion, the second element portion including a second magnetic element, a second magnetic member and a second opposing magnetic member, the second magnetic element including a second end portion and a second other end portion, a direction from the second end portion to the second other end portion being along the first direction, a direction from the portion of the first conductive member to the second magnetic element being along the second direction, a position of at least a part of the second magnetic element in the third direction being between a position of the second magnetic member in the third direction and a position of the second opposing magnetic member in the third direction, the third element unit including a third magnetic element, the third magnetic element including a third end portion and a third other end portion, the fourth element portion including a fourth magnetic element, the fourth magnetic element including a fourth end portion and a fourth other end portion, the first end portion being electrically connected to the third end portion, the first other end portion being electrically connected to the fourth end portion, the third other end portion being electrically connected to the second end portion, the second other end portion being electrically connected to the fourth other end portion, and the third magnetic element and the fourth magnetic element not overlapping the first magnetic member, the first opposing magnetic member, the second magnetic member, and the second opposing magnetic member in the second direction.

19. The sensor according to claim 18, further comprising a circuit portion, the circuit portion including a first circuit, a second circuit and a third circuit, the first circuit being configured to supply a first current including an AC component between the first conductive portion and the first other conductive portion, the second circuit being configured to supply an element current or an element voltage between a first connection point of the first end portion and the third end portion and a second connection point of the second other end portion and the fourth other end portion, and the third circuit being configured to output a signal corresponding to an electrical signal generated between a third connection point of the third other end portion and the second end portion and a fourth connection point of the first other end portion and the fourth end portion.

20. An inspection device, comprising:
the magnetic sensor according to claim 1; and
a processor configured to process an output signal obtained from the magnetic sensor.

* * * * *